(12) United States Patent
Carniato et al.

(10) Patent No.: US 6,391,904 B1
(45) Date of Patent: May 21, 2002

(54) IMINOGUANIDINE DERIVATIVES, PREPARATION METHOD, USE AS MEDICINES

(75) Inventors: Denis Carniato, Cagnes sur Mer; Jean-Francois Gourvest, Claye-Souilly; Jean-Marie Ruxer, Issy les Moulineaux, all of (FR); Jochen Knolle, Kriftel; Anurschirwan Peyman, Kelkheim, both of (DE); Sarah C. Bodary, San Bruno; Thomas R. Gadek, Oakland, both of CA (US)

(73) Assignees: Aventis Pharma S.A. (FR); Genentech, Inc.

( * ) Notice: Subject to any disclaimer, the term of this patent is extended or adjusted under 35 U.S.C. 154(b) by 0 days.

(21) Appl. No.: 09/856,693

(22) PCT Filed: Nov. 23, 1999

(86) PCT No.: PCT/FR99/02880

§ 371 Date: Jun. 29, 2001

§ 102(e) Date: Jun. 29, 2001

(87) PCT Pub. No.: WO00/31044

PCT Pub. Date: Jun. 2, 2000

(30) Foreign Application Priority Data

Nov. 24, 1998 (FR) .............................. 98 14780

(51) Int. Cl.⁷ .................. A61K 31/4168; A61K 31/155; C07D 233/52; C07C 281/18; A61P 19/10

(52) U.S. Cl. .................... 514/392; 514/533; 548/331.5; 560/29

(58) Field of Search ........................ 548/331.5; 560/29; 514/392, 533

(56) References Cited

FOREIGN PATENT DOCUMENTS

| EP | 0820988 | 1/1998 |
|---|---|---|
| WO | 9734865 | 9/1997 |
| WO | 9736580 | 9/1997 |

*Primary Examiner*—Laura L. Stockton
(74) *Attorney, Agent, or Firm*—Bierman, Muserlian and Lucas

(57) ABSTRACT

A compound of the formula

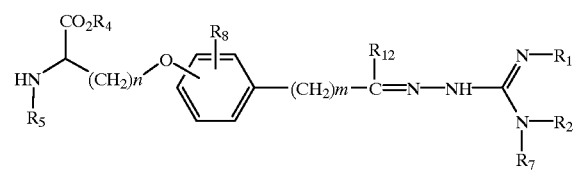

where the substituents are defined in the specification and its pharmaceutically acceptable salts and prodrugs thereof useful as antagonists of vitronectin receptors.

12 Claims, No Drawings

IMINOGUANIDINE DERIVATIVES, PREPARATION METHOD, USE AS MEDICINES

This application is a 371 of PCT/FR99/02880 filed Nov. 23, 1999.

A subject of the present invention is new iminogaunidine derivatives, their preparation process, their use as medicaments and the pharmaceutical compositions containing them.

A subject of the invention is the compounds of formula (I):

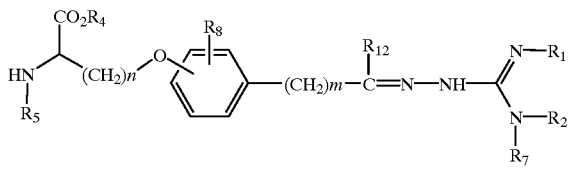

in which $R_1$, $R_2$, $R_3$, $R_4$, $R_5$, $R_7$, $R_8$ and $R_{12}$ have the meanings indicated below, their physiologically acceptable salts and their prodrugs. The compounds of formula (I) are compounds having a pharmacological activity and can therefore be used as medicaments. These are antagonists of the vitronectin receptor and inhibitors of cell adhesion and they inhibit bone resorption mediated by the osteoclasts. They are therefore useful for the therapeutic or prophylactic treatment of diseases which are caused at least in part by an undesirable increase in bone resorption, for example osteoporosis.

A subject of the invention is also the preparation process for the compounds of formula (I), their use, in particular as medicaments and the pharmaceutical compositions containing them.

The bone is constantly subjected to a dynamic process which includes bone resorption and bone formation. These processes are mediated via specialized cells. Bone format on is the result of the deposit of a mineral matrix by the osteoblasts and bone resorption is he result of the dissolution of this one matrix by the osteoclasts. The majority of bone disorders are caused by a disturbed equilibrium between bone formation and bone resorption. Osteoporosis is characterized by a dry loss of this bone matrix. As activated mature osteoclast resorbs the bone after adhesion to he bone matrix via the secretion of proteolytic enzyme, and protons inside the adhesion zone, resulting in depressions or hollows on the bone surface which appear when the osteoclast detaches itself from the bone.

Studies have shown that he fixation of the osteoclast on the bone is mediated by receptors: the integrins. Integrins are a superfamily of receptors mediating the cell/cell and more particularly cell/matrix adhesion process, including in particular $\alpha_{IIb}\beta_3$ as a blood platelet receptor (fibrinogen) and $\alpha_v\beta_3$ as vitronectin receptor.

The peptides containing the RGD unit as well as the anti $\alpha_v\beta_3$ antibodies are known for their ability to inhibit resorbtion of dentin and prevention of osteoclast adhesion on the mineralized matrices (Horton et al. Exp. Cell. Res. (1991), 195, 368). The peptide Echistatine, isolated from snake venom also contains an RGD unit and is described as an inhibitor of the adhesion of osteoclasts to the bone and is a powerful inhibitor of bone resorption in tissues cultured in vitro (Sato et al. J. Cell. Biol. (1990), 111, 1713) and in vivo in the rat (Fisher et al. Endocrinology (1993), 132, 1411).

The $\alpha_v\beta_3$ receptor is a transmembrane glycoprotein which is expressed in a large number of cells including endothelial cells, smooth muscle cells, osteoclast and cancerous cells which thus leads to a pluripotentiality of the compounds of formula (I) according to the invention.

In fact, the $\alpha_v\beta_3$ receptors expressed in the membrane of the osteoclasts are the basis of the adhesion/resorption process, contribute to the organization of the cell cytoskeleton, and are involved in osteoporosis. The $\alpha_v\beta_3$ receptors expressed in the smooth muscle cells of the aorta, stimulate their migration towards the neointima, which leads to the formation of arteriosclerosis and the occurrence of post-angioplastic recurrence of stenosis (Brown et al., cardiovascular Res. (1994), 28, 1815).

The endothelial cells secrete growth factors which are mitogens for the endothelium and can contribute to the formation of new blood vessels (Angogenesis).

The antagonists of $\alpha_v\beta_3$ integrin can therefore lead to a regression of cancerous tumors by inducing apoptosis of the angiogenic blood vessels. (Brook et al. Cell (1994) 79, 1157). Cheresh et al (Science 1195, 270, 1500) have described anti-$\alpha_v\beta_3$ antibodies or antagonists of the $\alpha_v\beta_3$ receptor which inhibit the process of angiogenesis induced by bFGF in the rat eye, a property which can be used for the treatment of retinopathies, in particular in diabetics.

The Patent Application WO-A-94/12181 describes aromatic or non-aromatic substituted systems and WO-A-94/08577 describes substituted heterocycles as antagonists of the fibrinogen receptor and inhibitors of platelet aggregation. EP-A-528 586 and EP-A-52858 describe phenylalanine derivatives substituted by an aminoalkyl or a heterocycle and WO-A-95/32710 describes aryl derivatives as inhibitors of bone resorption by the osteoclasts. WO-A-96/00574 describes benzodiazepines and WO-A-96/00730 describes compounds which inhibit the fibrinogen receptor, in particular benzodiazepines which are linked to a ring with 5 nitrogenous members as antagonists of the vitronectin receptor. DE-A-25 19654483 describes tyrosine derived antagonists of the vitronectin receptor. DE-A-19629816.4 claims cycloalkyl derivatives as antagonists of the vitronectin receptor. Other investigations have made it possible to show that the iminogaunidine derivatives of formula (I) show marked activity as inhibitors of the vitronectin receptor and of bone resorption mediated via the osteoclasts.

A subject of the invention is the compounds of formula

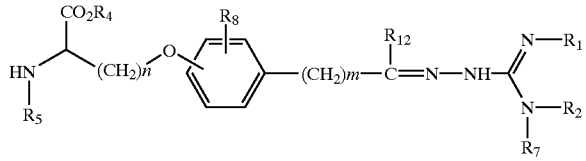

in which
either $R_1$ and $R_2$, independently from one another represent a hydrogen atom or an alkyl group containing 1 to 6 carbon. atoms non-substituted or substituted by $R_3$, or $R_1$ and $R_2$ together form a divalent alkylene radical containing 2 to 9 carbon atoms, saturated or unsaturated, such as —$(CH_2)p$— in which p is 2, 3, 4, 5, 6, 7, 8 or 9, non-substituted or substituted by one or more radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, the said divalent alkylene radical being able to be attached at the level of the carbon—carbon bond to a carbocycle or a heterocycle with 5 to 7 members, containing 1 or 2 nitrogen atoms, saturated or unsaturated, non-substituted or substituted by 1 or 2 $R_3$ radicals;

$R_3$ represents a $(C_1-C_8)$-alkyl, $(C_1-C_8)$-alkoxy, $(C_5-C_{14})$-aryl, $(C_5-C_{14})$-aryl-$(C_1-C_4)$-alkyl, halogen, trifluoromethyl, hydroxyl, nitro, amino, NH—$((C_1-C_4)$-alkyl), N$((C_1-C_4)$alkyl$)_2$, NHCO—$(C_1-C_4)$-alkyl or CO—$(C_1-C_4)$alkyl group;

$R_4$ represents either a hydrogen atom, or a $(C_1-C_6)$-alkyl—CO—O—$(C_1-C_4)$-alkyl or $(C_1-C_6)$-alkyl group, non-substituted or substituted by a radical chosen from hydroxyl, $(C_1-C_4)$-alkoxy, $(C_1-C_4)$-alkyl-$SO_2$, $NR_9R_9'$ and $N^+R_9R_9'R_9''Q^-$, in which $R_9$, $R_9'$ and $R_9''$ independently from one another, represent a hydrogen, a $(C_1-C_6)$-alkyl, $(C_5-C_{14})$-aryl or $(C_5-C_4)$-aryl-$(C_1-C_6)$-alkyl group and $Q^-$ is a physiologically acceptable anion, or one of the following radicals:

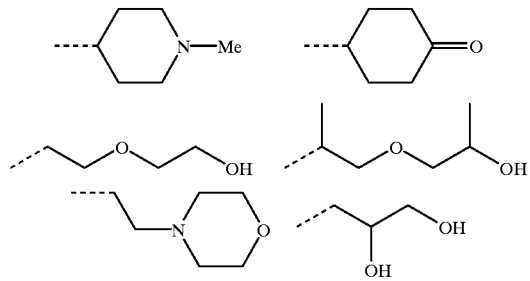

the dotted lines representing the position of the bond;

$R_5$ represents a hydrogen atom or a group chosen from $COR_6$, $CO_2R_6$, $SO_2R_6$, $SO_2NHCOR_6$, $SO_2NHCO_2R_6$, $CONH_2$ and $CONHR_6$ in which $R_6$ represents $(C_1-C_8)$-alkyl, $(C_6-C_{14})$-aryl, $(C_6-C_{14})$-aryl-$(C_1-C_6)$-alkyl, $(C_5-C_{14})$-heteroaryl or $(C_5-C_{14})$-heteroaryl-$(C_1-C_6)$-alkyl, $(C_3-C_{20})$(mono-, bi- or tri-)-cycloalkyl, $(C_3-C_{20})$(mono-, bi- or tri-)-cycloalkyl-$(C_1-C_6)$alkyl, the aryl or heteroaryl radical being non-substituted or substituted by 1, 2 or 3 $R_3$ radicals;

$R_7$ represents a hydrogen atom, $(C_1-C_6)$-alkyl-O—CO—, hydroxyl, $(C_1-C_6)$-alkyl-O—CO—O or nitro;

$R_8$ represents a hydrogen atom, halogen atom or an alkyloxy radical containing 1 to 6 carbon atoms;

$R_{12}$ represents a hydrogen atom or an alkyl radical containing 1 to 6 carbon atoms;

m is equal to 0, 1, 2 or 3;

n is an integer equal to 1, 2 or 3;

the said compounds of formula (I) being in all their possible isomer forms, alone or in a mixture of any ratio, the (alkyl) iminogaunidine group adjacent to the phenyl para or meta position of the oxygen, as well as their physiologically acceptable salts and their promedicaments (prodrugs).

All the radicals which can be found several times in the compounds of formula (I) for example the $R_3$ radical, are independant from one another and can be identical or different.

The alkyl radicals can be linear or branched, saturated or mono- or polyunsaturated. The also applies when they carry a substituent or when they represent a substituent of other radicals for example alkoxy, alkoxycarbonyl, aralkyl or heteroarylalkyl radicals.

By $(C_1-C_8)$-alkyl is meant the methyl, ethyl, propyl, butyl, pentyl, hexyl, heptyl, octyl, nonyl radicals, the n-isomers of these radicals, isopropyl, isobutyl, isopentyl, neopentyl, isohexyl, 3-methylpentyl, 2,3,4-trimethylhexyl, sec-butyl, tert-butyl, tert-pentyl. Among the preferred radicals methyl, ethyl, n-propyl, isopropyl, n-butyl, isobutyl, and tert-butyl can be mentioned.

The divalent alkylene radicals corresponding to the monovalent radicals mentioned above are for example the methylene, ethylene, 1,3-propylene, 1,2-propylene (=1-methylethylene), 2,3-butylene (=1,2-dimethylethylene), 1,4-butylene, or 1,6-hexylene radicals.

The unsaturated alkyl radicals are for example the alkenyl radicals such as vinyl, 1-propenyl, allyl, butenyl, 3-methyl-2-butenyl or the alkynyl radicals such as ethynyl, 1-propynyl or propargyl. By unsaturated divalent alkylene radicals is meant the alkenylene and alkynylene radicals which can also be linear or branched. They are for example vinylene, propenylene, ethynylene or propynylene radicals.

The cycloalkyl radicals can be monocyclic, bicyclic or tricyclic. They are for example cyclopropyl, cyclobutyl, cyclopentyl, cyclohexyl, cycloheptyl, cyclooctyl, cyclononyl, cyclodecyl, cycloundecyl, cycododecyl, cycloletradecyl or cyclooctadecyl radicals which can if appropriate be substituted for example by an alkyl containing 1 to 4 carbon atoms. As substituted cycloalkyl radicals, 4methyl-cyclohexyl and 2,3-dimethylecyclohexyl can be mentioned.

The bicycloalkyl and tricycloalkyl radicals can be non-substituted or substituted in any position, for example by one or more oxo groups and/or 1 or more identical or different alkyl groups such as methyl or isopropyl and preferably methyl alkyl groups. The junction bond of the bi or tricyclic radical can be situated in all positions of the molecule. The bond can be situated at the bridged carbon atom or one of the other carbon atoms. This bond can also take any position from the point of view of the stereochemistry, for example exo or endo. As an example of bicycloalkyl or tricycloalkyl radicals, camphanyl, bornyl, adamantyl such as 1-adamantyl or 2-adamantyl, caranyl, epiisobornyl, epibornyl, norbornyl or norpinanyl can be mentioned.

By halogen is meant fluorine, chlorine, bromine or iodine.

By the term $(C_5-C_{14})$-aryl is meant either the $(C_5-C_{14})$-aryl heterocyclic radicals $(=(C_5-C_{14})$-heteroaryl), in which the carbon atoms of the ring are replaced by a heteroatom such as nitrogen, oxygen or sulphur, or the carbocyclic $(C_6-C_{14})$-aryl radicals.

Among the carbocyclic $(C_6-Cl_{14})$-aryl radicals, phenyl, naphthyl, biphenylyl, anthryl or fluorenyl and more particularly 1-naphthyl, 2-naphthyl and phenyl can be mentioned.

Unless indicated to the contrary, the aryl radicals, in particular phenyl, can be non-substituted or substituted by one or more identical or different radicals chosen from $(C_1-C_8)$-alkyl, in particular $(C_1-C_4)$alkyl, $(C_1-C_8)$-alkoxy, halogen such as fluorine, chlorine and bromine, nitro, amino, trifluoromethyl, hydroxyl, methylenedioxy, cyano, hydroxycarbonyl, aminocarbonyl, $(C_{1-4})$-alkoxycarbonyl, phenyl, phenoxy, benzyl and benzyloxy. In general, 2 nitro groups at the most can be used in the compounds of formula (I) according to the invention.

In the case of monosubstituted phenyl, the substituent can be situated in position 2, 3 or 4, and preferably in position 3 or 4. In the case where the phenyl is di-substituted, the substituents car be in position 2, 3 or 2, 4 or 2, 5 or 2, 6 or 3, 4 or 3, 5. Preferably, in the di-substituted phenyls, the two substituents are in position 3, 4.

When this phenyl is tri-substituted the positions are the following: 2, 3, 4 or 2, 3, 5 or 2, 3, 6 or 2, 4, 5 or 2, 4, 6 or 3, 4. In the same way, the naphthyl radicals or other aryl radicals can be substituted in any position, or example the 1-naphthyl radical in position 2-, 3-, 4-, 5-, 6-, 7-, and 8 and the 2-naphthyl radical in position 1-, 3-, 4-, 5-, 6-, and 7. The ($C_5$–$C_{14}$)-aryl group can also represent a monocyclic or polycyclic aromatic system in which 1, 2, 3, 4 or 5 carbon atoms of the ring are replaced by heteroatoms, in particular, identical to or different from the group constituted by nitrogen, oxygen and sulphur. Among the heterocyclic ($C_5$–$C_{14}$)-aryl groups (=$C_5$–$C_{14}$)-heteroaryl) there can be mentioned the 2-pyridyl, 3-pyridyl, 4-pyridyl, pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl groups, or also benzo-condensed, cyclopenta-, cyclohexa-, or cyclohepta-condensed derivatives of these radicals. The heterocyclic system can be substituted by the same substituents mentioned above for the carbocyclic system.

Among the heteroaryl radicals, monocyclic or bicyclic aromatic systems having 1, 2 or 3 heteroatoms, in particular 1 or 2 heteroatoms are preferred, chosen from N, O or S, and which are non-substituted or substituted by groups such as ($C_1$–$C_6$)-alkyl, ($C_1$–$C_6$)-alkoxy, fluorine, chlorine, nitro, amino, trifluoromethyl, hydroxyl, ($C_1$–$C_4$)-alkoxycarbonyl, phenyl, phenoxy, benzyloxy, and benzyl.

Quite particularly, the monocyclic or bicyclic aromatic systems containing 5 to 10 members having 1 to 3 heteroatoms, in particular 1 or 2 heteroatoms, chosen from N, O and S and which can be substituted by 1 or 2 substituents such as ($C_1$–$C_4$)-alkyl, ($C_1$–$C_4$)-alkoxy, phenyl, phenoxy, benzyl and benzyloxy can be mentioned.

When $R_1$ and $R_2$ together form a divalent alkylene radical containing 2 to 9 carbon atoms, $R_1$ and $R_2$ form together with the two nitrogen atoms to which they are linked and the central carbon atom of the guanidine to which the two nitrogen atoms are linked, a 1,3-diazaheterocycle which is linked to the nitrogen atom in the $(CH_2)_m$—C=N—NH— group via its position 2.

As an example of 1,3-heterocycles which can be substituted as indicated at the level of the ($C_2$–$C_9$)-alkylene radical or the nitrogen atom of the guanidine, there can be mentioned the 2-imidazolyl radical, the 4,5-dihydro-2-imidazolyl radical, the 1,4,5,6-tetrahydro-2-pyrimidinyl radical or the 4,5,6,7-tetrahydro-1H-1,3-diazepin-2-yl radical.

In the case where a ring of 3 to 7 members is condensed at the level of the carbon-carbon bond of the ($C_2$–$C_9$)-alkylene radical, then $R_1$ and $R_2$ form together with the two nitrogen atoms to which they are linked and the central carbon atom of the guanidine to which the two nitrogen atoms are inked, a bicyclic heterocycle which is linked to the nitrogen atom, of the $(CH_2)_m$—CO—NH group and which can be substituted as indicated above.

The rings with 5 to 7 members condensed at the level of the carbon—carbon bond of the ($C_2$–$C_9$)-alkylene radical can be saturated, mono-unsaturated, di-unsaturated or aromatic; they can for example be cyclopropane, cyclohexane, cyclohexene, cyclohexadiene, cycloheptane or benzene Among the bicyclic aromatic systems linked to the nitrogen atom of the $(CH_2)_m$—C=N—NH— group, the 1,3a,4,5,6,6a-hexahydro-1,3-diazapentalen-2-yl radical, the 1H-2-benzimidazolyl radical, the 3a,4,5,6,7,7a-hexahydro-1H-benzymidazol-2-yl radical, the 4,5,6,7-tetrahydro-1H-benzimidazol-2-yl radical, the 4,7-dihydro-1-benzimidazole-2-yl radical or the 1H-imidazo[4,5-b]pyridin-2-yl radical can be mentioned.

In the case where the condensed ring is substituted and/or the ($C_2$–$C_9$)-alkylene radical is substituted, they are preferably mono- or di-substituted independently from one another by an identical or different $R_3$ radical. In the case where $R_1$ and/or $R_2$ are substituted alkyl groups, they are preferably mono- or substituted independently from one another by an identical or different $R_3$ radical.

The optically active carbon atoms contained in the compounds of formula (I) can independently from one another show the R configuration or the S configuration.

The compounds of formula (I) can be in the form of pure enantiomers or of pure diastereoisomers or in the form of a mixture of enantiomers, for example in the form of racemates or diastereoisomer mixtures.

A subject of the present invention is therefore pure enantiomers, mixtures of these enantiomers, pure diastereoisomers and mixtures of these diastereoisomers.

The invention relates to the mixtures of two or more than two stereoisomers formula (I) and all the ratios of these stereoisomers in the said mixtures. The compounds of formula (I) can, if appropriate, be present in the form of or Z isomers.

A subject of the invention is therefore pure E isomers, pure Z isomers and E/Z mixtures in any ratio.

The invention also relates to all the tautomer forms of the compounds of formula (I), relating for example to the form represented by formula (I), the form in which iminogaunidine is present in the form of a —N—N=C(NHR$_1$)(NR$_2$R$_7$) group and all the other forms which differ by the different position of the hydrogen atom are considered.

Finally, the invention relates to the different regioisomers linked to the para or meta position of the oxygen atom adjacent to the phenyl. They therefore include the following isomers: oxygen in position 4 and $R_8$ in position 3, oxygen in position 4 and $R_8$ in position 2, oxygen in position 3 and $R_8$ in position 4, oxygen in position 3 and $R_8$ in position 2, oxygen in position 3 and $R_8$ in position 5, oxygen in position 3 and $R_8$ in position 6. Preferably the oxygen is in position 4 and $R_8$ is in position 3. The diastereoisomers, including the E/Z isomers can be separated into individual isomers, for example by chromatography. The racemates can be separated into two enantiomers by current methods such as chiral chase chromatography or by resolution methods.

The physiologically acceptable salts of the compounds of formula (I) are in particular salts which can be used pharmaceutically or non-toxic salts, or salts which can be used physiologically.

When the compounds of formula (I) contain an acid group such as carboxylic acid, they are for example sats of alkali or alkaline-earth metals such as sodium, potassium, magnesium, calcium salts, and also the salts formed with physiologically acceptable quaternary ammonium ions and the addition salts with acids such as ammonia and physiologically acceptable organic amines such as for example triethylamine, ethanolamine or tris-(2-hydroxyethyl)amine.

When the compounds of formula (I) contain a basic group, they can form an addition salt with acids for example with inorganic acids such as hydrochloric, sulphuric, phosphoric acid or with organic carboxylic acids such as acetic, trifluoroacetic, citric, benzoic, maleic, fumaric, tartaric, methanesulphonic or para toluene sulphonic acid.

The compounds of formula (I) which comprise a basic group and an acid group, such as for example guanidino and carboxylic, can be present in the form of Zwiterions (betaines), which are also included in the present invention. The physiologically acceptable Q$^-$ anion which is contained in the compounds of formula (I) when $R_4$ is an alkyl radical substituted by a charged ammonium group, is preferably a monovalent anion or a polyvalent anion equivalent of an organic or inorganic, non-toxic, physiologically and in particular pharmaceutically acceptable acid, for example the anion or an anion equivalent of one of the acids mentioned above which can be used for the formation of the addition salts. $Q^-$ for example can be one of the anions (or anion equivalent) of a group chosen from chlorine, sulphate, phosphate, acetate, trifluoroacetate, citrate, benzoate, maleate, fumarate, tartrate, methanesulphonate and para-toluenesulphonate.

The salts of the compounds of formula (I) can be obtained by standard methods known to a person skilled in the art, or example by combining a compound of formula (I) with an organic or inorganic acid or a base in a solvent or a dispersant or from another salt by cation or anion exchange.

The invention also includes all the salts of the compounds of formula (I) which, because of their low physiological acceptability, cannot be used directly as medicaments, but can be used as intermediate products to implement the subsequent chemical modifications in the compounds of formula (I) or as starting products for the preparation of physiologically acceptable salts.

The present invention also includes all the solvates of the compounds of formula (I) for examples the hydrates, the solvates formed with alcohols, and all the derivatives of the compounds of formula (I), for example the esters, prodrugs and other physiologically acceptable derivatives, as well as the metabolites of the compounds of formula (I).

A more precise subject of the invention is the prodrugs of the compounds of formula (I) which can be converted to compounds of formula (I) in vivo under physiological conditions. The prodrugs of the compounds of formula (I), namely the chemically modified derivatives of the compounds of formula (I), are known to a person skilled in the art in order to obtain the improved properties in a desired fashion.

In order to have more information on the type of prodrug envisaged in the present invention, the following books can be mentioned: Fleicher et al., Advanced Drug Delivery Review 19 (1996) 115–130; Design of prodrugs, H. Bundgaard, Ed., Elsevier, 1985; H. Bungaard, Drugs of the Future 16 (1991) 443;

Saulnier et al. Bioorg. Med. Chem. Lett. 4 (1994) 1985; Safadi et al. Pharmaceutical Res. 10 (1993) 1350. Among the appropriate prodrugs of the compounds of formula (I) the following can preferably be mentioned:

the prodrugs in the form of esters of the carboxylic groups, in particular of the COOH group, when $R_4$ in $COOR_4$ is a hydrogen atom the prodrugs in the form of acyl and carbamate for the groups containing an acylable nitrogen such as the amino groups and in particular guanidine. In the acylated prodrugs or in the form of carbamate, a hydrogen atom situated on the nitrogen atom is replaced by an acyl group or carbamate, one or more times, for example twice. Among the preferred acyl groups or carbamates, the $R_{10}CO—$, $R_{11}OCO—$ groups, in which $R_{10}$ is a hydrogen or a $(C_1–C_{18})$-alkyl radical, $(C_3–C_{14})$-cycloalkyl, $(C_3–C_{14})$-cycloalkyl-$(C_1–C_8)$-alkyl, $(C_5C_{14})$-aryl groups, in which 1 to 5 carbon atoms can be replaced by heteroatoms such as N,O,S or $(C_5–C_{14})$-aryl-$(C_1–C_8)$alkyl, in which 1 to 5 carbon atoms in the aryl part can be replaced by heteroatoms such as N,O,S and R has the same values as $R_{10}$, with the exception of hydrogen can be mentioned.

In the compounds of formula (I), the $R_1$ and $R_2$ radicals preferably represent a hydrogen atom or together form a saturated or unsaturated divalent alkylene radical containing 2 to 5 carbon atoms and in particular 2 to 4 carbon atoms and more particularly 2 or 3 carbon atoms, the alkylene radical of which is non-substituted or substituted by one or two identical or different radicals chosen from halogen, $(C_1–C_6)$-alkyl, $(C_1–C_6)$-alkoxy, $(C_6–C_{14})$-aryl, $(C_6–C_{14})$-aryl-$(C_1–C_6)$alkyl, $(C_5–C_{14})$-heteroaryl, $(C_5–C_{14})$-heteroaryl-$(C_1–C_6)$-alkyl, $(C_3–C_{12})$-cycloalkyl and $(C_3–C_{12})$-cycloalkyl-$(C_1–C_6)$-alkyl and oxo, said divalent alkylene radical being able to be attached at the level of the carbon-carbon bond to a carbocycle or a heterocycle with 5 to 7 members, containing 1 or 2 nitrogen atoms, saturated or unsaturated, non-substituted or substituted by 1 or 2 $R_3$ radicals.

Among the compounds of formula (I), $R_1$ and $R_2$ preferably represent a nitrogen atom or a —$(CH_2)p$— group, in which p is 2, 3, 4 or 5, preferably 2, 3 or 4, more particularly 2 or 3, and which is non-substituted or substituted by one or two identical or different radicals chosen from halogen, $(C_1–C_6)$-alkyl, $(C_1–C_6)$-alkoxy, $(C_6–C_{14})$-aryl, $(C_6–C_{14})$-aryl-$(C_1–C_6)$alkyl, $(C_5–C_{14})$-heteroaryl, $(C_5–C_{14})$-heteroaryl-$(C_1–C_6)$-alkyl, $(C_3–C_{12})$-cycloalkyl and $(C_3–C_{12})$-cycloalkyl-$(C_1–C_6)$-alkyl and oxo, the said —$(CH_2)p$— radical being able to be attached at the level of the carbon-carbon bond to a carbocycle or a heterocycle with 5 to 7 members, containing or 2 nitrogen atoms, saturated or unsaturated, non-substituted or substituted by or 2 $R_3$ radicals.

$R_3$ is preferably an alkyl or alkoxy group containing 1 to 4 carbon atoms.

$R_4$ is preferably a hydrogen atom or an alkyl group containing 1 to 6 carbon atoms non-substituted or substituted by a group chosen from $(C_1–C_4)$-alkoxy, $(C_1–C_4)$-alkyl-$SO_2$ and $NR_9R_9'$ in which $R_9$ and $R_9'$ independently from one another represent a hydrogen atom or $(C_1–C_4)$-alkyl. $R_4$ is quite particularly a hydrogen atom or an alkyl group containing 1 to 4 carbon atoms non-substituted or substituted by the radicals mentioned above.

$R_5$ is preferably a hydrogen atom or a $CO_2R_6$, $SO_2R_6$, $SO_2NHR_6$ or $SO_2NHCO_2R_6$ group $R_5$ is preferably a $(C_1–C_8)$-alkyl or naphthyl radical, non-substituted or substituted by $R_3$, a mono- bi- or tri-cycloalkyl radical containing 3 to 12 carbon atoms or $(C_3–C_{12})$(mono-, bi- or tri-)-cycloalkyl-$(C_1–C_6)$-alkyl or the radical of formula (II)

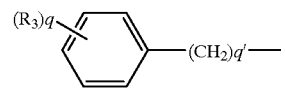

in which the $R_3$ radicals can be identical or different, and can be situated at any position of the phenyl radical, q is equal to 0.1, 2 or 3, preferably 0 or 1 and more particularly 0 and q' is equal to 0 or 1.

$R_6$ more particularly represents an alkyl radical containing to 4 carbon atoms, a phenyl radical mono, bi or trisubstituted by $(C_1–C_6)$-alkyl, a naphthyl radical, an adamantylmethyl radical or the radical of formula (II) in which a is 0 or 1. $R_6$ quite particularly represents the radical of formula (II) with q equal to 0 or 1 and q' equal to 1, that is to say a benzyl radical non-substituted or monosubstituted in ortho, meta or para position by $R_3$.

$R_7$ is preferably a hydrogen atom or an alkyloxycarbonyl group containing 2 to 7 carbon atoms, more particularly hydrogen or alkyloxy-carbonyl containing 2 to 5 carbon atoms and quite particularly hydrogen.

$R_8$ is preferably a hydrogen, fluorine or methoxy atom and more particularly a hydrogen atom.

$R_{12}$ is preferably a hydrogen or methyl atom.

The preferred compounds of formula (I) are the compounds in which one or more radicals have the preferred meanings. A particular subject of the invention is a compound of formula (I')

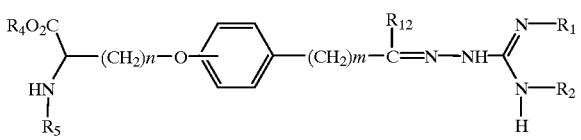

in which $R_1$ and $R_2$ represent a hydrogen atom or together form a saturated or unsaturated divalent alkylene radical containing 2 to 5 carbon atoms or more particularly represent a hydrogen atom or together form a —$(CH_2)p$— group, in which p is 2, 3, 4 or 5, preferably 2, 3 or 4, more particularly 2 or 3, said alkylene radical or —$(CH_2)p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$ cycloalkyl and $(C_3-C_{12})$-cycloalkyl-$(C_1-C_6)$-alkyl and oxo, said alkylene or —$(CH_2)p$— group being able to be attached at the level of the carbon-carbon bond to a carbocycle or a heterocycle containing 1 or 2 nitrogen atoms, of 5 to 7 members, saturated or unsaturated, non-substituted or substituted by $R_3$ and in particular by 1 or 2 $R_3$ radicals;

$R_3$ represents an alkyl or alkyloxy group containing 1 to 6 carbon atoms;

$R_4$ represents a hydrogen atom or an alkyl group containing 1 to 6 carbon atoms non-substituted or substituted by a group chosen from $(C_1-C_4)$-alkoxy, $(C_1-C_4)$-alkyl-$SO_2$ and $NR_9R_9'$ in which $R_9$ and $R_9'$ independently from one another represent a hydrogen atom or $(C_1-C_4)$-alkyl, $R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl radical, non-substituted or substituted by $R_3$, a cycloalkyl radical containing 3 to 12 carbon atoms or $(C_3-C_{12})$-cycloalkyl-$(C_1-C_6)$-alkyl or the radical of formula (II)

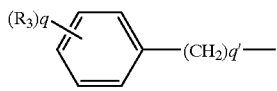

in which the $R_3$ radicals can be identical or different, and can be situated at any position of the phenyl radical, q and q' are equal to 0 or 1;

$R_{12}$ represents a hydrogen atom or an alkyl radical containing 1 to 6 carbon atoms;

m is equal to 0, 1, 2 or 3, n is an integer equal to 1, 2 or 3, said compounds of formula (I') being in all their possible isomer forms, alone or in a mixture in any ratio, the (alkyl) iminoguanidine group adjacent to the phenyl being in para or meta position of the oxygen as well as their physiologically acceptable salts and their prodrugs.

A more particular subject of the invention is also a compound of formula (I'), in which, $R_1$ and $R_2$ represent a hydrogen atom or together form a saturated or unsaturated divalent alkylene radical containing 2 to 4 carbon atoms or more particularly represent a hydrogen atom or together form a —$(CH_2)p$— group, in which p is 2, 3 or 4, said alkylene radical or —$(CH_2)p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, the said alkylene or —$(CH_2)p$— group being able to be attached at the level of the carbon-carbon bond to a carbocycle or a heterocycle containing 1 or 2 nitrogen atoms, with 5 to 7 members, saturated or unsaturated, non-substituted or substituted by $R_3$ and in particular by 1 or 2 $R_3$ radicals;

$R_3$ represents an alkyl or alkyloxy group containing from 1 to 6 carbon atoms;

$R_4$ represents a hydrogen atom or an alkyl group containing from 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a $(C_1-C_8)$-alkyl or naphthyl group, non-substituted or substituted by $R_3$, a cycloalkyl radical containing 3 to 12 carbon atoms or $(C_3-C_{12})$-cycloalkyl-$(C_1-C_6)$alkyl or the radical of formula (II)

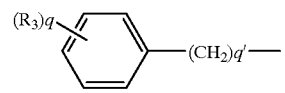

in which the $R_3$ radicals can be identical or different, and can be situated at any position of the phenyl radical, q and q' are equal to 0 or 1;

$R_{12}$ represents a hydrogen atom of an alkyl radical containing 1 to 6 carbon atoms;

m is equal. to 0, 1, 2 or 3;

n is an integer equal to 1, 2 or 3;

said compounds of formula (I) being in all their possible isomer forms, alone or in a mixture in any ratio, the (alkyl) iminoguanidine group adjacent to the phenyl in para or meta position of the oxygen as well as their physiologically acceptable salts and their prodrugs.

A more particular subject of the invention is also a compound of formula (I'), in which, $R_1$ and $R_2$ represent a hydrogen atom or together form a saturated or unsaturated divalent alkylene radical containing 2 to 3 carbon atoms or more particularly represent a hydrogen atom or together form a —$(CH_2)p$— group, in which p is 2 or 3, said alkylene radical or —$(CH_2)p$— group being non-substituted or substituted by one or two identical or different radicals chosen from halogen, $(C_1-C_6)$-alkyl, $(C_1-C_6)$-alkoxy, $(C_6-C_{14})$-aryl, $(C_6-C_{14})$-aryl-$(C_1-C_6)$alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, the said alkylene or —$(CH_2)p$— group being able to be attached at the level of the carbon-carbon bond to a carbocycle or a heterocycle containing 1 or 2 nitrogen atoms, with 5 to 7 members, saturated or unsaturated, non-substituted or substituted by $R_3$ and in particular by 1 or 2 $R_3$ radicals;

$R_3$ represents an alkyl or alkyloxy group containing from 1 to 6 carbon atoms;

$R_4$ represents a hydrogen atom or an alkyl group containing 1 to 6 carbon atoms;

$R_5$ represents a hydrogen atom, a $CO_2R_6$, $SO_2R_6$, $SO_2NHR_6$ or $SO_2NHCO_2R_6$ group in which $R_6$ is a ($C_1$–$C_8$)-alkyl or naphthyl radical, non-substituted or substituted by $R_3$, a cycloalkyl radical containing 3 to 12 carbon atoms or ($C_3$–$C_{12}$)-cycloalkyl-($C_1$–$C_6$)-alkyl or the radical of formula (II)

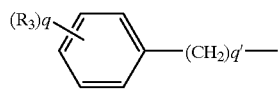

in which the $R_3$ radicals can be identical or different, and can be situated at any position of the phenyl radical, q and q' are equal to 0 or 1;

$R_{12}$ represents a hydrogen atom or an alkyl radical containing 1 to 6 carbon atoms;

m is an integer equal to 0, 1 or 2;

n is an integer equal to 2;

said compounds of formula (I) being in all their possible isomer forms, alone or in a mixture in any ratio, the (alkyl) iminoguanidine group adjacent to the phenyl being in para or meta position of the oxygen as well as their physiologically acceptable salts and their prodrugs.

Among the preferred compounds of formula (I), are the compounds in which the asymmetrical carbon carrying the $CO_2R_4$ and $NHR_5$ groups is of S configuration.

A quite particular subject of the invention is the compounds of formula (I) or (I') as defined above in which $R_5$ is a $CO_2R_6$ radical, $R_6$ being as defined above and in particular —$CH_2Ph$, —$C(CH_3)_3$ and $CH_2$-Adamantyl, said compounds of formula (I) being in all their possible isomer forms, alone or in a mixture in any ratio, the (alkyl) iminoguanidine group adjacent to the phenyl being in para or meta position of the oxygen, as well as their physiologically acceptable salts and their prodrugs.

A quite particular subject of the invention is the compounds of formula (I) or (I') as defined above in which $R_5$ is a $SO_2R_6$ radical, $R_6$ being as defined above and in particular an alkyl containing 1 to 6 carbon atoms, naphthyl and phenyl substituted by one or more alkyl radicals containing 1 to 6 carbon atoms or a $CF_3$ group, the said compounds of formula (I) being in all their possible isomer forms, alone or in a mixture in any ratio, the (alkyl) iminoguanidine group adjacent to the phenyl being in para or meta position of the oxygen, as well as their physiologically acceptable salts and their prodrugs.

A more particular subject of the invention is the compounds of formula (I) or (I') as defined above in which $R^5$ is an $SO_2NHR_6$ or $SO_2NHCO_2R_6$ radical, $R_6$ being as defined above and in particular —$CH_2Ph$, —$C(CH_3)$ and $CH_2$-Adamantyl, the said compounds of formula (I) being in all their possible isomer forms, alone or in a mixture in any ratio, the (alkyl) iminoguanidine group adjacent to the phenyl being in para or meta position of the oxygen, as well as their physiologically acceptable salts and their prodrugs.

A subject of the invention is also the compounds of formula (I) the names of which follow:

O-[4-[3-[(4,5-dihydro-1H-imidazol-2-yl)hydrazono] butyl]-phenyl]-N-[(phenylmethoxy)carbonyl]-homoserine, O-[4-[3-[(aminoiminomethyl)hydrazono]phenyl]-N-[(phenylmethoxy)carbonyl]-homoserine, O-[4-[3-[(4,5-dihydro-1H-imidazol-2-yl)hydrazono] propyl]-phenyl]-N-[(phenylmethoxy)carbonyl]-homoserine, O-[4-[3-[(aminoiminomethyl)hydrazono]propyl]phenyl]-N-[(phenylmethoxy)carbonyl]-homoserine, O-[4-[2-[(4,5-dihydro-1H-imidazol-2-yl)hydrazono] propyl]-phenyl]-N-[(phenylmethoxy)carbonyl]-homoserine, O-[4-[2-[(4,5-dihydro-1H-imidazol-2-yl)hydrazono] propyl]-2-methoxyphenyl]-N-[(phenylmethoxy) carbonyl]-homoserine, O-[4-[2-[(4,5-dihydro-1H-imidazol-2-yl)hydrazono] propyl]-2-fluorophenyl]-N-[(phenylmethoxy) carbonyl]-homoserine, O-[3-[3-[(aminoiminomethyl)hydrazono]butyl]phenyl]-N-[(phenylmethoxy)carbonyl]-homoserine, O-[3-[3-[(4,5-dihydro-1H-imidazol-2-yl)hydrazono] butyl]-phenyl]-N-[(phenylmethoxy)carbonyl]-homoserine, O-[3-[2-[(4,5-dihydro-1H-imidazol-2-yl)hydrazono] propyl]-phenyl]-N-[(phenylmethoxy)carbonyl]-homoserine, O-[3-[3-[(aminoiminomethyl)hydrazono]propyl]phenyl]-N-[(phenylmethoxy)carbonyl]-homoserine, O-[3-[3-[(4,5-dihydro-1H-imidazol-2-yl)hydrazono] propyl]-phenyl]-N-[(phenylmethoxy)carbonyl]-homoserine, O-[4-[(4,5-dihydro-1H-imidazol-2-yl)hydrazono] methyl]-phenyl]-N-[(phenylmethoxy)carbonyl]-homoserine, as well as their physiologically acceptable salts and their prodrugs.

A subject of the present invention is also a process for the preparation of the compounds of formula (I). The compounds can generally be prepared, for example during convergent synthesis by coupling two or more fragments which can be derived by retrosynthesis of the compounds of formula (I). In order to avoid the functional groups leading to undesirable or secondary reactions during each stage of synthesis, it can be advantageous or necessary during synthesis to introduce the functional groups in the form of precursors which are subsequently converted to desired functional groups or to temporarily block the functional groups by implementing a protective group strategy suitable for the synthesis which is known to a person skilled in the art (Greene, Wuts protective Group in Organic Synthesis, Wiley 1991).

The compounds of formula (I) can therefore be prepared, for example, by coupling an acyl or formyl of formula (III) in a manner known per se

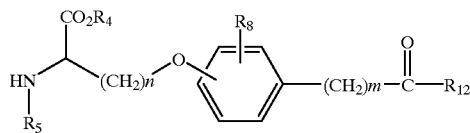

in which $R_4$, $R_5$, $R_8$, $R_{12}$, n and m are as defined above for formula (I), and where, if appropriate, the functional groups are in the form of precursors or in protected form, with an aminoguanidine or an aminoguanidine derivative of formula (IV)

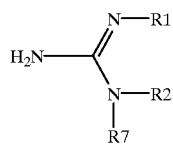

in which $R_1$, $R_2$ and $R_7$ are as defined above in formula (I), and where, if appropriate, the functional groups are in the form of precursors or in protected form, said functional groups optionally present in the form of precursor or in protected form, being subsequently converted into groups present in the compounds of formula (I).

In addition, the free guanidines of formula (IV), the aminoguanidine salts can also be used in the reaction with the compounds of formula (III), the free aminoguanidines being formed in-situ or in a separate stage by means of a base.

The reaction of an activated carboxylic acid derivative of formula (III) with the aminoguanidine (or derivative) of formula (IV) is carried out in a manner known per se either in a solvent or in an organic protic, out inert solvent. In this case solvents such as ethanol or butanol are used. The reaction mixture is then treated and if desired the reaction product is purified according to the methods known to a person skilled in the art.

The protective groups optionally present in the compounds obtained from the compounds of formula (III) and (IV) are then eliminated by standard methods; for example, the tert-butyl ester groups are converted to carboxylic acid by treatment with trifluoroacetic acid, the benzyl groups are eliminated by hydrogenation or the fluorenylmethoxycarbonyl groups are also eliminated in the presence of secondary amine and other reactions are carried out using standard methods, for example acylation reactions. If necessary, the conversion into physiologically acceptable salts is carried out by methods known to a person skilled in the art.

When $R_5$ represents a hydrogen atom, the functionalization of the amine to a group present in the compounds of formula (I), i.e. in particular when $R_5$ represents a $CO_2R_6$, $SO_2R_6$, $SO_2NHR_6$ or $SO_2NHCO_2R_6$ group is carried out at the level of in the compounds of formulae (III) or (I) and preferably (III). For example in order to obtain the compounds of formula (III) with $R_5=CO_2R_6$ from the corresponding amine a compound of formula X'—$CO_2R_6$ is reacted, X' being a parting group and in particular O-succinic or also a halogen. In order to obtain the compounds of formula (III) with $R_5=SO_2R_6$ from the corresponding amine a compound of formula $R_6SO_2X'$ is reacted, X' being in particular a halogen. In order to obtain the compounds of formula (III) with $R_5=SO_2NHCO_2R_6$ from the corresponding amine a compound of formula $X'SO_2NHCO_2R_6$ is reacted, X' being in particular a halogen, or preferably by the action of an isocyanate of formula $ClSO_2NCO$ in the presence of an $R_6$—OH alcohol. Finally in order to obtain the compounds of formula (III) with $R_5=SO_2NHR_6$ from the corresponding amine a $ClSO_2NCO$ type isocyanate is firstly reacted in the presence of a terbutyl alcohol, then a halide of formula $R_6X$ and finally a deprotection agent of the BOC group.

The starting compounds of formula (III) and (IV) which are then linked in order to produce the compounds of formula (I) are commercially available, and can be prepared according to the methods described in literature or also are accessible by analogy. The preparation of the compounds of formula (III) is illustrated in the diagram described below, it being understood that the present invention is not restricted to these syntheses or these starting products. It is not a major difficulty for a person skilled in the art to envisage modifications to the syntheses described in our Application for the preparation of other compounds of formula (I) according to the invention. Therefore the compound of formula (V) which is commercially available can be condensed with a halogenated derivative of formula (VI) (described in Arch. Pharm. (1995) 328, 367) in order to produce a compound of formula (VII). This condensation can be carried out for example in the presence of a base such as cesium carbonate in acetonitrile or any other medium encouraging the nucleophilic substitutions known to a person skilled in the art. The compound of formula (VII) is an example of a compound of formula (III) in which $R_{12}$ is a methyl.

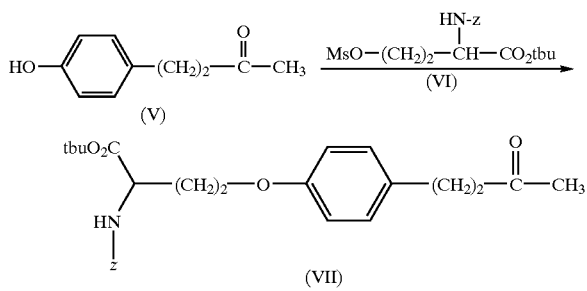

The compounds of formula (I) are compounds having a pharmacological activity and can therefore be used as medicaments in the treatment or the prevention of bone disease, tumorous diseases as well as cardiovascular disorders.

The compounds of formula (I) as well as their physiologically acceptable salts and their prodrugs can be administered to animals, preferably to mammals and in particular to human beings as therapeutic or prophylactic medicaments. They can be administered as they are or in a mixture with one or more other compounds of formula (I) or also in the form of a pharmaceutical preparation (pharmaceutical composition) which allows enteral or parenteral administration and which contains an effective dose of at least one compound of formula (I) and/or its physiologically acceptable salts and/or its prodrugs as active ingredient as well as current and pharmaceutically inert supports and/or additives.

A subject of the present invention is therefore the compounds of formula (I) and/or their physiologically acceptable salts and/or their prodrugs as medicaments.

A subject of the present invention is also the use of the compounds of formula (I) and/or their physiologically acceptable salts and/or their prodrugs for the preparation of medicaments intended for the prevention or the treatment of the diseases mentioned above or below, for example for the treatment or prevention of bone diseases.

A subject of the present invention is also the pharmaceutical compositions which permit enteral or parenteral administration and which, contain an effective dose of at least one compound of formula (I) and/or its physiologically acceptable salts and/or its prodrugs as active ingredient as well as one or more usual pharmaceutically inert supports and if appropriate one or more usual additives.

The medicaments can be administered orally, for example in the form of pills, tablets, coated tablets, film-encased, granules, gelatin capsules and soft capsules, solutions, syrups, emulsion, suspension or aerosol mixture.

Administration can however be carried out by rectal route, for example in the form of suppositories or by parenteral route, for example in the form of injectable solutions or infusions, microcapsules or implants, or by percutaneous route, for example in the form of an ointment, solutions, pigments or colorants, or by another route such as in the form of an aerosol or nasal spray.

The pharmaceutical compositions according to the invention are prepared according to methods known per se, organic or inorganic, pharmaceutically inert supports being added to the compounds of formula (I) and/or their physiologically acceptable salts and/or their prodrugs. For the production of pills, tablets, coated tablets and hard gelatin capsules, it is possible for example, to use lactose, corn starch or its derivatives, talc, stearic acid or its salts, etc. Suitable supports for soft gelatin capsules or suppositories are for example fats, waxes, semi-solid or liquid polyols, natural or modified oils etc. Appropriate vehicles for the preparation of solutions, for example injectable solutions, emulsions or syrups are for example water, alcohol, glycerol, polyols, sucrose, inverted sugars, glucose, vegetable oils, etc.

Suitable supports for the microcapsules or the implants are for example glyoxilic acid and lactic acid copolymers. The pharmaceutical preparations normally contain 0.5% to 90% by weight of the compounds of formula (I) and/or their physiologically acceptable salts. In addition to the active ingredients and the supports, the pharmaceutical preparations can contain additives such as for example diluting agents, disintegration agents, binding agents, lubricants, wetting agents, stabilisers, emulsifiers, preservatives, sweetening agents, coloring flavouring or aromatizing agents, thickeners, buffering agents, and solvents or solubilizing agents or agents to obtain a delayed release effect and also salts to modify the osmotic pressure, coating agents or antioxidants.

They can also contain two or several compounds of formula (I) and/or their physiologically acceptable salts and/or their prodrugs. Moreover, in addition to at least one or more compounds of formula (I) and/or their physiologically acceptable salts and/or their prodrugs, they can contain at least one or more other active ingredients which can be used for therapeutic or prophylactic uses. The pharmaceutical preparations (pharmaceutical compositions) normally contain 0.2 to 500 mg, and preferably 1 to 200 mg of the compound of formula (I) and/or their physiologically acceptable salts and/or their prodrugs.

The compounds of formula (I) are quite particularly antagonists of vitronectin receptors and are therefore capable for example of inhibiting the adhesion of osteoclasts on the surface of the bone and therefore bone resorption by the osteoclasts. The action of the compounds of formula (I) can be demonstrated for example in a test in which the inhibition of the binding of vitronectin to the cells which contain the vitronectin receptor is determined. Further information about this test is given below.

As antagonists of the vitronectin receptor, the compounds of formula (I) and their physiologically acceptable salts and their prodrugs are in general suitable for the treatment or prevention of diseases linked to the interactions between the vitronectin receptors and their ligands, in the process of cell—cell or cell-matrix interaction or which can be influenced by the inhibition of interactions of this type, to relieve or cure when an inhibition of interactions of this type is desired. As explained at the beginning, such an interaction plays an important role in bone resorption, in angiogenesis or in the proliferation of smooth muscle vascular cells. Bone diseases in which the treatment or prevention require the use of the compounds of formula (I), are in particular osteoporosis, hypercalcemia, osteopenia, for example caused by bony metastases, dental disorders for example parodontitis, hyperparathyroidism, periarticular erosions in rheumatoid arthritis, and Paget's disease. Moreover the compounds of formula (I) can be used to relieve, prevent or treat bone disorders which are caused by treatments, by glucocorticoids, therapies linked to taking steroids or corticosteroids or by male or female sex hormone deficiencies. All these disorders are characterized by bone loss, which is caused by a lack of equilibrium between bone formation and bone destruction and which can be favourably influenced by the inhibition of bone resorption by the osteoclasts. Besides this use as inhibitor of bone resorption mediated via the osteoclasts, the compounds of formula (I) and their physiologically acceptable salts and their prodrugs are used as inhibitors of tumorous growth or cancerous metastases, in the treatment of inflammatory disorders, for the therapy or prophylaxis of cardiovascular disorders, such as arteriosclerosis or the recurrence of stenosis, or the therapy or prophylaxis of nephropathy or retinopathy such as for example diabetic retinopathy.

The compounds according to the invention can also have an activity vis-á-vis other integrins which interact with their ligand via the tripeptide sequence RGD ($\alpha_v\beta_1$, $\alpha_v\beta_5$, $\alpha_{IIB}\beta_3$), giving them properties which can be used pharmacologically to treat the pathologies associated with these receptors.

This activity vis-á-vis the integrins therefore makes the compounds of formula (I) of use in the prevention or treatment of numerous diseases such as those mentioned above or in Dermot Cox's review DN§P 8(4) May 1995, 197–205 the content of which is incorporated in the present Application.

When the compounds of formula (I) are used, the doses can vary within wide limits and must be set according to the person treated. This depends for example on the compound used or the nature and severity of the disease to be treated, if the conditions are serious or chronic or if a prophylactic treatment is used. In the case of administration by oral route, the daily dose in general varies from 0.01 to 100 mg/kg and preferably from 0.1 to 50 mg/kg, in particular from 0.1 to 5 mg/kg. For example for an adult weighing 75 kg a daily dose can be envisaged varying from 0.3 to 0.5 mg/kg.

In the case of administration by intravenous route, the daily dose varies approximately from 0.01 to 100 mg/kg and preferably from 0.05 to 10 mg/kg. The daily dose can be divided, in particular in the case of the administration of a large quantity of active ingredient, in several, for example 2, 3 or 4 parts. If appropriate, depending on individual behaviour, it may be necessary to administer different increasing or decreasing doses.

Apart from the use of the compounds of formula (I) as medicaments, their use as a vehicle or support for active ingredients in order to transport these active ingredients in a specific manner towards a target (Drug targeting, see Targeted Drug Delivery, R C Juliano, Handbook of Experimental Pharmacology, Vol 100, Ed. Born, G. V. R. et al, Springer Verlag). The active ingredients which can be transported are in particular those used for the treatment or prevention of the diseases mentioned above.

The compounds of formula (I) and their salts can also be used as a diagnostic agent, for example for in vitro methods or as an auxiliary in biochemical studies in which blocking the vitronectin receptor or influencing the cell—cell or cell-matrix interactions are desired. They can moreover be used as an intermediate for the preparation of other compounds, in particular other active ingredients, which are accessible from the compounds of formula (I), for example by modification or introduction of radicals or functional groups.

EXAMPLES

The products were identified by mass spectrometry (MS), infrared (IR) and/or NMR spectrometry. The compounds, which were purified by chromatography using a eluent which contains for example acetic or trifluoroacetic acid, and which are then dried or in which during the last stage of synthesis, trifluoroacetic acid for example was used to eliminate a tert-butyl protective group, sometimes containing, depending on the manner in which the product was dried, the acid originating from the eluent or from the last stage of synthesis and therefore is partially or completely in the form of the salt of the acid used, for example in the form of a salt of acetic or trifluoroacetic acid. They can also be more or less hydrated. Abbreviations/chemical names: PCC: pyridine chlorochromate; DMF: dimethylformamide; PTSA: paratoluene sulphonic acid; THF: tetrahydrofuran; MeOH: methanol; AcOEt: ethyl acetate; TFA: trifluoroacetic acid; TEA: triethylamine; sh. (Shoulder); S (strong); s (singlet); d (doublet); t (triplet); b (broad); m (muliplet).

Example 1

O-[4-[3-[(4,5-Dihydro-1H-imidazol-2-yl)hydrazono]butyl]-phenyl]-N-[(phenylmethoxy)carbonyl]-homoserine.

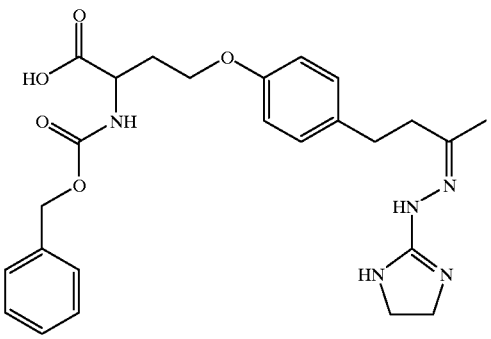

Stage A: Ethyl O-[4-(3-Oxobutyl)phenyl]-N-[phenylmethoxy)carbonyl]-homoserinate

The mixture constituted by 580 mg of 4-(4-hydroxyphenyl)-2-butanone (commercial) 1.47 g of ethyl 4-bromo-2-[[(phenylmethoxy)carbonyl]amino]butanoate and 2.67 g of cesium carbonate $Cs_2CO_3$ in 50 ml of acetonitriles is heated under reflux for 1 hour 30 minutes, the $Cs_2CO_3$ is filtered, washed with dichloromethane then evaporated under reduced pressure until of 1.6 g of crude product is obtained which is purified by chromatography on a silica column (Kieselgel 60; 40–63 μm) eluting with a cyclohexane/ethyl acetate mixture 7/3. 900 mg of expected product is obtained.

IR ($CHCl_3$); 3429 $cm^{-1}$ (=C—NH); 1717 $cm^{-1}$ (max. C=O complex); 1612, 1585, 1512 $cm^{-1}$ (Aromatic+amide II).

Stage B: Ethyl O-[4-[3-[(4,5-Dihydro-1H-imidazol-2-yl)hydrazono]butyl-]phenyl]-N-[(phenylmethoxy)carbonyl]-homoserinate The mixture constituted by 430 mg of the ketone prepared in Stage A, 549 mg of 4,5-dihydro-1H-imidazol-2-yl-hydrazine hydrobromide in 20 ml of butanol is heated at the temperature of 110° C. for 2 hours then evaporated under reduced pressure until 1.1 g of crude product is obtained which is purified by chromatography (Kieselgel 60, 40–63 μm) eluting with a dichloromethane/methanol mixture 90/10. 500 mg of expected product is obtained.

IR ($CHCl_3$); 3446 $cm^{-1}$ (NH+associated); 1738 (sh.), 1720 $cm^{-1}$ (max.); (C=O); 1675 (S), 1605, 1587, 1512 $cm^{-1}$ (C=N+Aromatic+amide II).

Stage C: O-[4-[3-[(4,5-Dihydro-1H-imidazol-2-yl)hydrazono]butyl]-phenyl]-N-[(phenylmethoxy)carbonyl]-homoserine 1 ml of 2N soda is added to a solution of 500 mg of the ester prepared in the previous stage in 5 ml of ethanol and heated under reflux for 30 minutes. After evaporation under reduced pressure, an oil is obtained which is taken up in water and which is neutralized by adding 1N hydrochloric acid. The reaction medium is again evaporated under reduced pressure and 640 mg of a crude product is obtained a part of which (150 mg) is purified by chromatography (Kieselgel 60, 40–65 μm) eluting with a $CH_2Cl_2$/methanol mixture (80/20). 30 mg of expected product is obtained in the form of an E/Z mixture 95/5 Rf ($CH_2Cl_2$/MeOH/$H_2O$/AcOH 88/12/1/1)=0.25

IR (Nujol); 3340, 3245 $cm^{-1}$ (OH/NH); 1714, 1701, 1662 $cm^{-1}$ (CO); 1611, 1580, 1546, 1513 $cm^{-1}$ (Conjuguated system+Aromatic amide II).

NMR ($CD_3OD$); 1.94 (s) 1.98 (s) $CH_3$—C=N; 2.03 (m, 1H) 2.34 (m, 1H) $CH_2$ central; 2.62 (m, 2H) 2.83 (m, 2H) =C—$CH_2$—$CH_2$—C=; 3.73 (s); 3.78 (s) 4H N—$CH_2$—$CH_2$—N; 4.03 (t, 2H, Ph—O—$CH_2$—$CH_2$—); 4.23 (m, 1H, —CH($CO_2H$) (NHZ)); 5.07 (AB, $CO_2CH_2Ph$); 6.81 and 7.1,0; (AA'BB', Ph—O); 7.32 (m, aromatic 5H);

Example 2

O-[4-[3-[(Aminoiminomethyl)hydrazono]butyl]phenyl]-N-[(phenylmethoxy)carbonyl]-homoserine

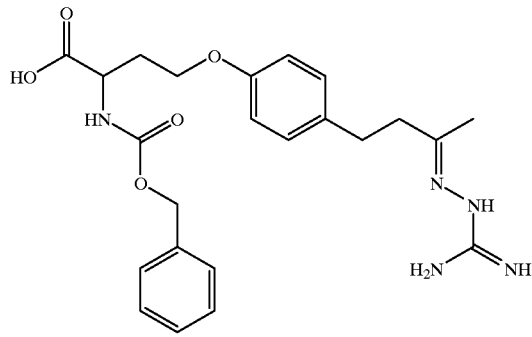

The operation is carried out as in Example 1 Stages A, B and C but using 440 mg of ketone (obtained in Stage A of Example 1) and 342 mg of aminoguanidine hydrochloride. 380 mg of expected product is obtained after chromatography (eluent $CH_2Cl_2$/MeOH/$H_2O$/AcOH 90/10/1/1) in the form of an E/Z mixture 85/15.

IR (Nujol); Absorption OH/NH region; 1700–1675 $cm^{-1}$ (C=O); 1612, 1585, 1510 $cm^{-1}$ (C=N+C=O+aromatic+amide II).

NMR (DMSO); 1.92 (s) 2.01 (s) $CH_3$—C=N; 2.08 (m, 1H) 2.32 (m, 1H central $CH_2$; 2.62 (t) 2.85 (t) =C—$CH_2$—$CH_2$—C=; 4.02 (t, 2H, Ph—O—$CH_2$—$CH_2$—); 4.32 (m, —CH($CO_2H$) (NHZ)); 5.07 (AB, $CO_2CH_2Ph$); 6.81 and 7.08 (AA'BB', Ph—O); 7.30 (m, aromatic 5H).

Example 3

O-[4-[3-[(4,5-Dihydro-1H-imidazol-2-yl)hydrazono]propyl]-phenyl]-N-[(phenylmethoxy)carbonyl]-homoserine

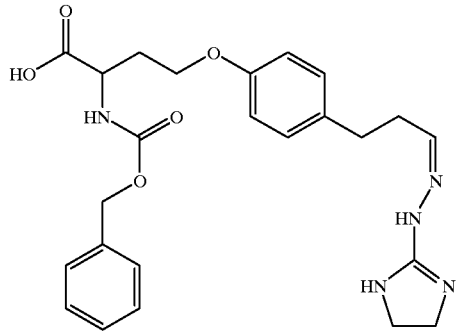

The operation is carried out as in Example 1 Stages A, B and C but using 190 mg of 3-(4-hydroxyphenyl)-propanal and 530 mg of ethyl 4-bromo-2-[[(phenylmethoxy)carbonyl]amino]butanoate (Stage A) then, during Sage B, 92 mg of 4,5-dihydro-1H-imidazol-2-yl-hydrazine hydrobromide. 20 mg of expected product is obtained in the form of an E/Z mixture 90/10.

NMR (DMSO); 1.98 (m, 1H) 2.15 (m, 1H) central $CH_2$; 2.44 (m, 2H) 2.68 (m, 2H) =C—$CH_2$ and $CH_2$—Ph; 3.29 to 3.55 N—$CH_2$—$CH_2$—N; 3.97 (m, Ph—O—C$\underline{H}_2$—$CH_2$— and CH); 5.01 (bs, $CO_2C\underline{H}_2$Ph); 6.60 to 7.20 (aromatic and CH=N); 7.34 (bs, aromatic); 6.92 (H mobile).

Example 4

O-[4-[3-[(Aminoiminomethyl)hydrazono]propyl]phenyl]-N-[(phenylmethoxy)carbonyl]-homoserine

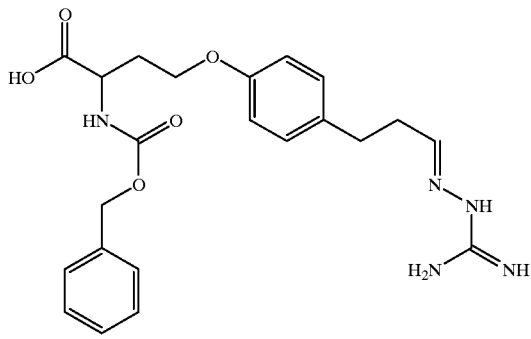

The operation is carried out as in Example 2 stages A, B and C but using 190 mg of 3-(4-hydroxyphenyl)-propanal and 530 mg of ethyl 4-bromo-2-[[(phenylmethoxy)carbonyl]amino]butanoate Stage A). 20 mg of expected product is obtained in the form of an E/Z mixture 75/25.

NMR (DMSO); 1.98 (m, 1H) 2.11 (m, 1H) central $CH_2$; 2.43 (m, 2H) 2.65 (m, 2H) =C—$CH_2$—$CH_2$—C=; 3.97 (t, 2H) 3.89 (m, 1H) (Ph—O—$C\underline{H}_2$—$CH_2$— and $C\underline{H}(CO_2H)$ (NHZ); 5.00 (s, $CO_2C\underline{H}_2$Ph); 6.81 and 7.20, 6.81 and 7.18 (AA'BB' resolved aromatic); 7.34 (m, aromatic); 7.38 (t, partially masked =C$\underline{H}$—$CH_2$); 7.0 to 8.0 (m, mobile broad H's);

Example 5

O-[4-[2-(4,5-Dihydro-1H-imidazol-2-yl)hydrazono]propyl]-phenyl]-N-[(phenylmethoxy)carbonyl]-homoserine

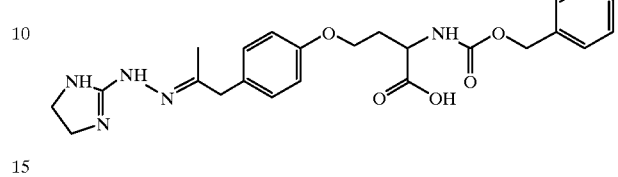

The operation is carried out as in Example 1 Stages A, B and C but using 800 mg of 3-(4-hydroxyphenyl)-2-propanone and 1.83 g of ethyl 4-bromo-2-[[(phenylmethoxy)carbonyl]amino]butanoate (Stage A) then, during Stage B, 718 mg 4,5-dihydro-1H-imidazol-2-yl-hydrazine hydrobromide. The saponificaton stage is carried out in the presence of soda in methanol. 180 mg of expected product is obtained in the form of an E/Z mixture 80/20.

NMR (DMSO); 1.72 (s) 1.76 (s) $CH_3$—C=; 1.97 (m, 1H) 2.09 (m, 1H, central $CH_2$; 3.42 (s) 3.47 (s) =C—$CH_2$—C=; 3.55 (bs) 3.68 (s) N—$CH_2$—$CH_2$—N; 3.88 to 4.05 (m, 3H Ph—O—$C\underline{H}_2$—$CH_2$—+$C\underline{H}(CO_2H)NHZ$)); 4.99 (s, $CO_2C\underline{H}_2$Ph); 6.72 6.79 7.04 7.08 (aromatic AA'BB'); 6.92 (bd) 6.58 (m) COCHNH; 7.33 (m, aromatic 5H); 7.94 (m, mobile broad H).

Example 6

O-[4-[2-[(4,5-Dihydro-1H-imidazol-2-yl)hydrazono]propyl]-2-methoxyphenyl]-N-[(phenylmethoxy)carbonyl]-homoserine

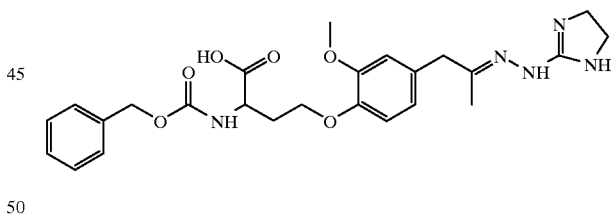

The operation is carried out as in Example 1 Stages A, B and C but using 900 mg of 3-(4-hydroxy-3-methoxyphenyl)-2-propanone and 1.80 g of ethyl 4-bromo-2-[[(phenylmethoxy)carbonyl]amino]butanoate (Stage A) then, during Stage B, 1.47 g of 4,5-dihydro-1H-imidazol-2-yl-hydrazine hydrobromide. The saponificaton stage is carried out in the presence of soda in methanol. 20 mg of expected product is obtained in the form of an E/7 mixture 90/10

NMR (DMSO); 1.90 $H_3C$—C=N; 1.90 to 2.10 central $CH_2$; 3.43 2H Ph—$CH_2$—C=N; 3.57 =N—$CH_2$; 3.67 (s) Ph—OMe; 3.97 (m, 3H; Ph—O—$C\underline{H}_2$—$CH_2$—+C$\underline{H}(CO_2H)NHZ$)); 5.00 (bs, $CO_2C\underline{H}_2$Ph); 6.69 (dd) 6.75 (d, J=1.5); 6.80 (d, J=9) (aromatic); 7.07 (d, =C—NH—CH); 7.33 (b, aromatic); 7.95 (spread, mobile H).

Example 7

O-[4-[2-[(4,5-Dihydro-1H-imidazol-2-yl)hydrazono]propyl]-2-fluorophenyl]-N-[(phenylmethoxy)carbonyl]-homoserine

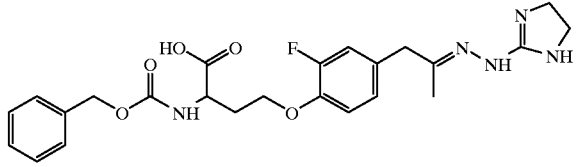

The operation is carried out as in Example 1 Stages A, B and C but using 515 mg of 3-(3-fluoro-4-hydroxyphenyl)-2-propanone and 1.05 g of ethyl 4-bromo-2-[[phenylmethoxy)carbonyl]amino]-butanoate (Stage A) then, during Stage B, 0.517 g of 4,5-dihydro-1H-imidazol-2-yl-hydrazine hydrobromide. The saponificaton stage is carried out in the presence of soda in methanol. 680 mg of expected product is obtained in the form of an E/Z mixture 80/20.

NMR (DMSO); 1.72 (s) 1.78 (s) C$\underline{H}_3$—C=; 1.99 to 2.11 central CH$_2$; 3.44 (s); 3.50 (s) =C—CH$_2$—C=; 3.58 (bs) 3.69 (s) N—CH$_2$—CH$_2$—N; 3.95 (m, C$\underline{H}$(CO$_2$H)NHZ)); 4.07 (t, broad) Ph—O—CH$_2$—CH$_2$—; 5.00 (s, CO$_2$C$\underline{H}_2$Ph); 6.90 to 7.07 (m, aromatic 3H); 7.33 (m, aromatic 5H); 7.96 (m) 10.22 (bs) H mobile.

Example 8

O-[3-[3-[(Aminoiminomethyl)hydrazono]butyl]phenyl]-N-[(phenylmethoxy)carbonyl]-homoserine

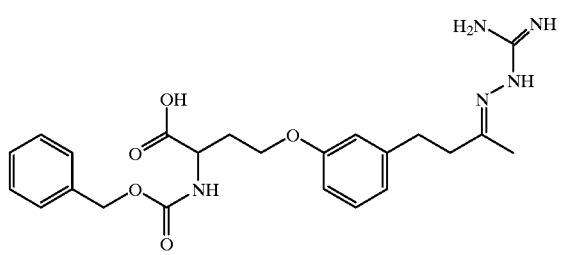

The operation is carried out as in Example 1 Stages A, B and C but using 390 mg of 4-(3-hydroxyphenyl)-2-butanone and 818 mg of ethyl 4-bromo-2-[[(phenylmethoxy)carbonyl]amino]butanoate (Stage A). 180 mg of expected product is obtained. (MP=95–100° C.) in the form of an E/Z mixture 50/50.

NMR (DMSO); 1.90 (s) 1.91 (s) =C—CH$_3$; 2.05 (m) CH2 central; 2.55 (m, partially masked) 2.79 (t,<2H) =C—CH$_2$—CH$_2$—C=; 3.98 (m, 3H); (Ph—O—C$\underline{H}_2$—CH$_2$— and C$\underline{H}$(CO$_2$H) (NHZ); 5.01 (s, CO$_2$C$\underline{H}_2$Ph); 6.69 (m, 2H) 6.80 (dl, 1H) 7.16 (t, 1H) (aromatic); 7.34 (m, aromatic 5H); 7.74 (m, mobile broad H's).

Example 9

O-[3-[3-[(4,5-Dihydro-1H-imidazol-2-yl)hydrazono]butyl]-phenyl]-N-[(phenylmethoxy)carbonyl]-homoserine

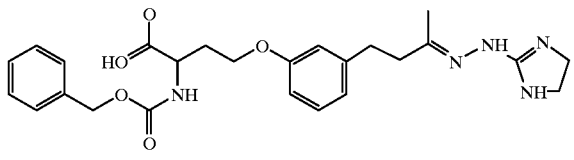

The operation is carried out as in Example 1 Stages A, B and C but using 390 mg of 4-(3-hydroxyphenyl)-2-butanone and 818 g of ethyl 4-bromo-2-[[(phenylmethoxy)carbonyl]amino]butanoate (Stage A) then, during Stage B, 380 mg of 4,5-dihydro-1H-imidazol-2-yl-hydrazine hydrobromide. The saponification stage is carried out in the presence of soda in methanol. 110 mg of expected product is obtained in the form of an E/Z mixture 45/55.

NMR (DMSO) 1.87 (s) 1.89 (s) (CH$_3$—C=); 2.09 (m, central CH$_2$; 2.78 (m) 2.40 to 2.60 masked =C—CH$_2$—CH$_2$—C=; 3.49 (bs) =N—CH$_2$—; 3.80 to 4.10 (3H Ph—O—C$\underline{H}_2$—CH$_2$—+C$\underline{H}$(CO$_2$H)NHZ)); 5.0 (s) 5.04 (s), CO$_2$C$\underline{H}_2$Ph); 6.66 (s1) H2; 6.53 to 6.80 (H5 and H6); 6.87 (d); =C—NH—CH; 7.15 (m, H4); 7.35 (m, broad 5H, aromatic).

Example 10

O-[3-[2-[(4,5-Dihydro-1H-imidazol-2-yl)hydrazono]propyl]-phenyl]-N-[(phenylmethoxy)carbonyl]-homoserine

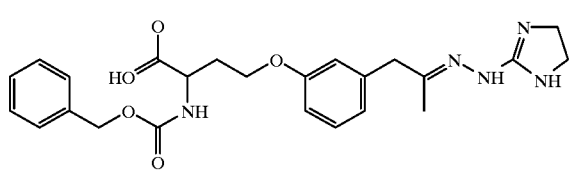

The operation is carried out as in Example 1 Stages A, B and C but using 100 mg of 4-(3-hydroxyphenyl)-2-propanone and 240 mg of ethyl 4-bromo-2-[[(phenylmethoxy)carbonyl]amino]butanoate (Stage A) then, during Stage B, 131 mg of 4,5-dihydro-1H-imidazol-2-yl-hydrazine hyrobromide. The saponificaton stage is carried out in the presence of soda in methanol. 50 mg of expected product is obtained in the form of an E/Z mixture.

NMR (DMSO) 1.71 (s) 1.83 (s)(CH$_3$—C=); 1.95 to 2.15 (m, central CH$_2$); 3.45 (bs) Ph—CH$_2$C=N—; 3.53(s), 3.58 (s,b) =N—C$\underline{H}_2$; 3.98 (ml, Ph—O—CH$_2$; +C$\underline{H}$(CO$_2$H) (NHZ)); 4.99 (bs, CO$_2$C$\underline{H}_2$—Ph); 6.63 to 6.76 (3H); 6.89 (bs) 7.07 (t) 7.17 (dd, 1H) aromatic H's; 7.00 (d, =C—N$\underline{H}$—CH)

Example 11

O-[3-[3-[(Aminoiminomethyl)hydrazono]propyl]phenyl]-N-[(phenylmethoxy)carbonyl]-homoserine

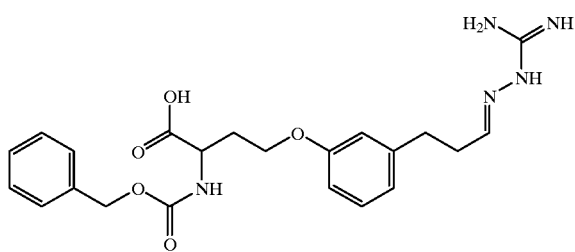

Stage A: Ethyl O-[4-(3-Hydroxypropyl)phenyl]-N-[(phenylmethoxy)carbonyl]-homoserinate.

The mixture constituted by 306 mg of 4-hydroxybenzenepropanol, 770 mg of ethyl 4-bromo-2-[[(phenylmethoxy)carbonyl]amino]butanoate and 740 mg of $Cs_2CO_3$ in 10 ml of acetonitrile is heated under reflux for 45 minutes, the solid is filtered, washed with dichloromethane then the filtrate is evaporated under reduced pressure until 1.5 g of crude product is obtained which is purified by chromatography on a silica column (Kieselgel 60; 40–63 μm) eluting with a dichloromethane/methanol mixture 95/5. 440 mg of expected product is obtained.

IR ($CHCl_3$) 3624 cm$^{-1}$ (—OH); 3431 cm$^{-1}$ (NH); 721 cm$^{-1}$ (max. C=O); 1609, 1602, 1584, 1508 cm$^{-1}$ (Aromatic+amide II).

Stage 3: Oxidation ethyl O-[4-(3-oxopropyl)phenyl]-N-[(phenylmethoxy)carbonyl]-homoserinate

245 mg of the alcohol prepared in the previous stage and 254 mg of PCC in 3 ml of dichloromethane are mixed for 30 minutes at ambient temperature, then 126 mg of additional PCC is added and the reaction medium is agitated for 15 minutes. The reaction medium is evaporated under reduced pressure until 800 mg of crude product is obtained which is purified by chromatography eluting with an ethyl acetate/cyclohexane mixture 1/1. 100 mg of expected product is obtained.

IR ($CHCl_3$) 3432 cm$^{-1}$ (NH); 1724 cm$^{-1}$ (max. C=O); 1610, 1602, 1585, 1508, 1492 cm$^{-1}$ (Aromatic+amide II).

Stage C: Condensation ethyl O-[3-[3-[(aminoiminomethyl)hydrazono]propyl]phenyl]-N-[(phenylmethoxy)carbonyl]-homoserinate

The mixture constituted by 302 mg of the aldehyde prepared in Stage B, 248 mg of aminoguanidine hydrochloride in 5 ml of butanol to which a few crystals of PTSA are added is heated at a temperature of 110° C. for 15 minutes, then evaporated under reduced pressure until 500 mg of crude product is obtained which is purified by chromatography Kieselgel 60, 40–63 μm) eluting with a dichloromethane/methanol mixture 90/10. 265 mg of expected product is obtained.

IR ($CHCl_3$) 3466, 3432 cm$^{-1}$+associated (NH/NH2 region); 1736 (sh.), 1721 cm$^{-1}$ (max.) (C=O); 1675 (S, C=N); 1636, 1610, 1602, 1585, 1508, 1489 cm$^{-1}$ (C=N+Aromatic+$NH_2$+amide II).

Stage D: Saponification O-[3-[3-[(aminoiminomethyl)hydrazono]propyl]phenyl]-N-[(phenylmethoxy)carbonyl]-homoserine

560 μl of 2N soda is added to a solution of 255 mg of the ester prepared in the previous stage in 5 ml of ethanol and the reaction medium is heated under reflux for 15 minutes. After evaporation under reduced pressure, 320 mg of a crude product is obtained which is purified by chromatography (Kieselgel 60, 40–65 μm) eluting with a dichloromethane/methanol/water/acetic acid mixture 90/10/1/1. 125 mg of expected product is obtained in the form of an E/Z mixture.

IR (Nujol) 3466, 3337 cm$^{-1}$, Absorption OH/NH region+ general absorption; 1697 cm$^{-1}$ (C=O); 1675 cm$^{-1}$ (C=N); 1636, 1609, 1584, 1533, 1487 cm$^{-1}$ (C=N+Aromatic+ amide II).

NMR (DMSO) 2.05 (central $CH_2$); 2.49 (masked) 2.78 (m) =C—$CH_2$—$CH_2$—C=N; 3.93 (q, C$\underline{H}$($CO_2H$)(NHZ)); 4.06 (m, Ph—O—$C\underline{H}_2$); 5.02 (bs, $CO_2C\underline{H}_2$Ph); 6.69 (dt) 6.76 (bd) H4 and H6; 6.74 (bs, H2); 7.15; (t, H5); 7.35 (l, aromatic H and NH); 7.48 (t, —N=C$\underline{H}$—$CH_2$).

Example 12

O-[3-[3-[(4,5-Dihydro-1H-imidazol-2-yl)hydrazono]propyl]-phenyl]-N-[(phenylmethoxy)carbonyl]-homoserine

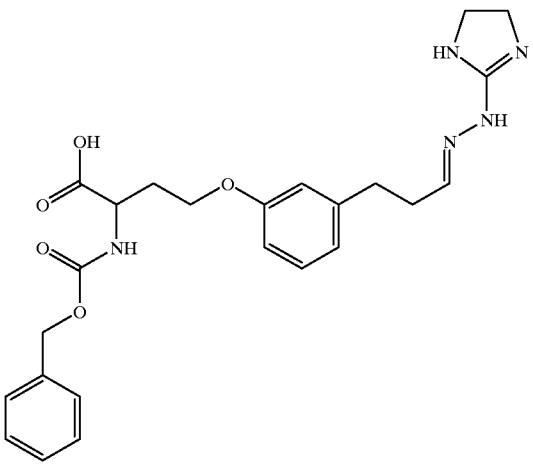

The operation is carried out as in Example 11 Stages A, B, C and D but using 4,5-dihydro-1H-imidazol-2-yl-hydrazine hydrobromide in Stage C.

IR (Nujol) Absorption OH/NH region; 1700 cm$^{-1}$ (C=O); 1675, 1600, 1582, 1486 cm$^{-1}$ (C=N+Aromatic+ amide II).

NMR (DMSO); 2.00 to 2.15 ($CH_2$ central); 2.60 to 3.65 8H =C—$C\underline{H}_2$ and =N—$C\underline{H}_2$; 3.92 (b, 1H, C $\underline{H}$($CO_2H$)(NHZ)); 4.05 (m b, Ph—O—$C\underline{H}_2$); 5.02 (s); 5.04 (s), $CO_2C\underline{H}_2$Ph; 6.60 to 6.95 (3H) 7.15 (m, 1H) aromatic H; 7.35 (b, —N=C$\underline{H}$—$CH_2$ and $\underline{Ph}$—$CH_2$).

Example 13

O-[4-[(4,5-Dihydro-1H-imidazol-2-yl)hydrazono]methyl]phenyl]-N-[(phenylmethoxy)carbonyl]-homoserine

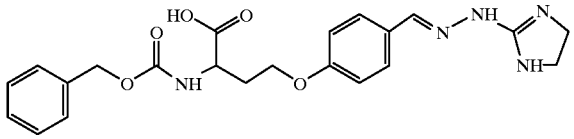

Stage A: Ethyl O-[4-(Hydroxymethyl)phenyl]-N-[(phenylmethoxy)carbonyl]-homoserinate

The mixture constituted by 690 mg of 4-hydroxybenzenethanol, 1.72 g of ethyl 4-bromo-2-

[[(phenylmethoxy)carbonyl]amino]butanoate and 1.63 g of Cs$_2$CO$_3$ in 100 ml of acetonitrile is heated under reflux or 45 minutes, the solid is filtered, washed with dichloromethane then the filtrate is evaporated under reduced pressure until 2.6 g of crude product is obtained which is purified by chromatography on a silica column (Kieselgel 60; 40–63 μm) eluting with a dichloromethane/methanol mixture 9/5. 1.58 g of expected product is obtained.

IR (CHCl$_3$); 3618 cm$^{-1}$ (—OH); 3434 cm$^{-1}$ (NH); 1721 cm$^{-1}$(max. C═C); 1610, 1582, 1512 cm$^{-1}$(Aromatic+amide II).

Stage B: Oxidation Ethyl O-[4-formylphenyl]-N-[(phenylmethoxy)carbonyl]-homoserinate 31 g of the alcohol prepared in the previous stage and 1.41 g of PCC in 30 ml of dichloromethane are mixed together for 1 hour at ambient temperature, evaporated under reduced pressure until 800 mg of crude product is obtained and purified by chromatography eluting with an ethyl acetate/cyclohexane mixture 1/1. 575 mg of product is obtained corresponding to obtaining 4-formylphenyl instead of the expected 4-formylmethylphenyl.

IR (CHCl$_3$); 3424 cm$^{-1}$ (NH); 721, 1699 cm$^{-1}$ (C═O); 1601.1580.1510 cm$^{-1}$ (Aromatic+amide II).

Stage C: Condensation Ethyl O-[4-[(4,5-Dihydro-1H-imidazol-2-yl)hydrazono]methyl]phenyl]-N-[(phenylmethoxy)carbonyl]-homoserinate.

The mixture constituted by 160 mg of the aldehyde prepared in Stage A, 83 mg of 4,5-dihydro-1H-imidazol-2-yl-hydrazine hydrobromide in 23 ml of butanol to which a few crystals of PTSA are added is heated to a temperature of 110° C. for 15 minutes, then evaporated under reduced pressure until 253 mg of crude product is obtained which is purified by chromatography (Kieselgel 60, 40–63 μm) eluting with a dichloromethane/methanol/ammonium hydroxide mixture 90/10/1. 190 mg of expected product is obtained.

IR (CHCl$_3$); 3449 cm$^{-1}$ (NH); 1721 cm$^{-1}$ (C═O); 1638, 1608, 1595, 1568, 1511 cm$^{-1}$ (C═N Aromatic+amide II).

Stage D: Saponification O-[4-[(4,5-Dihydro-1H-imidazol-2-yl)hydrazono]methyl]phenyl]-N-[(phenylmethoxy)carbonyl]-homoserine 0.36 ml of 2N soda is added to a solution of 168 mg of the ester prepared in the previous stage in 20 ml of methanol and heated under reflux for 30 minutes. After evaporation under reduced pressure, 170 mg of a crude product is obtained which is purified by chromatography (Kieselgel 60, 40–3 μm) eluting with a dichloromethane/methanol/water/acetic acid mixture 85/15/1/1. 150 mg of expected product is obtained.

Melting point=132° C.

IR (Nujol); General absorption OH/NH; 1670 cm$^{-1}$ (C═O); 1604, 1572, 1510 cm$^{-1}$ (conjuguated system+Aromatic+amide II).

NMR (DMSO) 2.02 (m) 2.13 (m) CH$_2$ central; 3.47 (bs, 4H N—C$\underline{H}_2$—C$\underline{H}_2$—N; 3.93 (m, bt after exchange), C$\underline{H}$(CO$_2$H)(NHZ)); 6.97 (bd) 7.08 (d); mobile CH(CO$_2$H) (N $\underline{H}$Z); 4.04 (t, 2H, Ph—O—C$\underline{H}_2$); 5.01 (bs, CO$_2$C$\underline{H}_2$Ph); 6.88 and 7.57 (AA' BB' phenyl); 7.34 (m, aromatic 5H+mobile 1H); 7.88 (t, —N═C$\underline{H}$—C═).

Pharmacological Test: Kistrin/Vitronectin Receptor (α$_v$β$_3$) ELISA Test Protocol:

96-well MaxiSorp plates are coated overnight at 40 C with 100 μl of Kistrin at 1 μg/ml (dilution in coating buffer: 0.05M carbonate)/NaOH pH 9.6. The next day, the wells are emptied and the ligands (kistrin) are then fixed (fixation buffers: PBS containing 0.5% BSA (pH=7.4)) for 1 hour at ambient temperature under gentle agitation of 125 rpm. The wells are washed six times (washing buffer: PBS containing 0.05% Tween 20 (pH 7.7) then the following is added per well and in this order:

- 40 μl of incubation buffer
- 10 μl of the dilution of the product to be tested (the products are diluted in a 50:50 DMSO/water mixture)
- 50 μl of human α$_v$β$_3$ receptor (cf Pytel et al. Methods Enzymol. (1987) 144 (Dilution in incubation buffer, adapted according to the batch of receptor and according to the ligand). The ligand, the α$_v$β$_3$ receptor and the products to be studied are incubated for 3 hours at ambient temperature with gentle agitation of 125 rpm.

The wells are again washed six times, then incubated for 2 hours at ambient temperature with mild agitation of 125 rpm, in the presence of 100 μl of anti-receptor antibody coupled to a peroxidase (The 4B12-HRP antibody is diluted in incubation buffer (50 mM TRIS pH 7.4; 0.5% BSA; 0.05% Tween 20; 1 mM MnCl$_2$; 50 μM CaCl$_2$; 50 μM MgCl$_2$; 100 mM NaCl). The dilution is to be adapted according to the batch of receptor.

The wells are then washed six times before measurement of the ligand-receptor bond is carried out using a peroxidase developer kit (TBM Microwell Peroxidase Substrate System Kirkegaard; Ref cat 50-76-00).

This kit contains a flask A of substrate (3,3',5,5'-tetramethylebenzidine at 0.4 g/l) and a flask B (H$_2$O$_2$ to 0.02% in Citrate/Citric acid). Extemporaneously, one volume of A is mixed with one volume of B, then the reaction mixture is distributed at a rate of 100 μl/wells.

The enzymatic reaction develops between 6 to 10 minutes for Kistrin/α$_v$β$_3$ then its development is stopped by the addition of 100 μl of 1M phosphoric acid. The optical density is determined at 450 nm.

Expression of the Results

The following curve is plotted: the bond percentage as a function of the logarithm of each concentration of the tested product.

For each product IC50 is determined according to the following formula: IC50=(B0+Bmin)/2 B0=Maximum bond in the absence of any product Bmin=Minimum bond in the presence of the highest concentration of the product.

| Example | K/VnR IC50 (μM) |
|---|---|
| ex 1 | 0.15 |
| ex 2 | 1.35 |
| ex 3 | 0.11 |
| ex 4 | 0.45 |
| ex 5 | 0.022 |
| ex 6 | 0.012 |
| ex 7 | 0.022 |
| ex 9 | 2 |
| ex 10 | 0.355 |
| ex 11 | 3.25 |
| ex 12 | 0.96 |
| ex 13 | 0.292 |

What is claimed is:

1. A compound of the formula

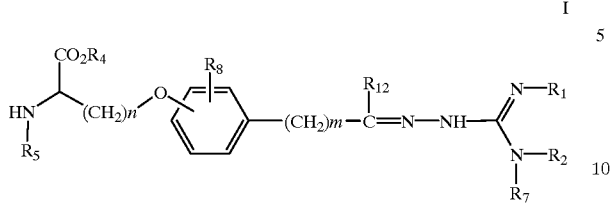

wherein $R_1$ and $R_2$ are independently hydrogen or alkyl of 1 to 6 carbon atoms, unsubstituted or substituted by $R_3$, or $R_1$ and $R_2$ together form a divalent alkylene of 2 to 9 carbon atoms, saturated or unsaturated, unsubstituted or substituted by at least one member of the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_4)$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said divalent alkylene being able to be attached by a carbon—carbon bond to a carbocycle or a heterocycle with 5 to 7 members, containing 1 or 2 nitrogen atoms, saturated or unsaturated, unsubstituted or substituted by 1 or 2 $R_3$ $R_3$ is selected from the group consisting of $(C_1-C_8)$-alkyl, $(C_1-C_8)$-alkoxy, $(C_5-C_{14})$-aryl, $(C_5-C_{14})$-aryl-$(C_1-C_4)$-alkyl, halogen, trifluoromethyl, hydroxy, nitro, amino, —NH—$((C_1-C_4)$-alkyl, —N$((C_1-C_4)$-alkyl$)_2$, —NHCO—$(C_1-C_4)$-alkyl or —CO—$(C_1-C_4)$-alkyl group;

$R_4$ is selected from the group consisting of a) hydrogen, b) $(C_1-C_6)$-alkyl-CO—O—$(C_1-C_4)$-alkyl and $(C_1-C_6)$-alkyl, unsubstituted or substituted by a member selected from the group consisting of hydroxyl, $(C_1-C_4)$-alkoxy, $(C_1-C_4)$-alkyl-SO$_2$, —NR$_9$R$_9$' and —N$^+$R$_9$R$_9$'R$_9$"Z$^-$, wherein R$_9$, R$_9$' and R$_9$" are independently selected from the group consisting of hydrogen, $(C_1-C_6)$-alkyl, $(C_5-C_{14})$-aryl and $(C_5-C_{14})$-aryl-$(C_1-C_6)$-alkyl and Q is a physiologically acceptable anion, and c)

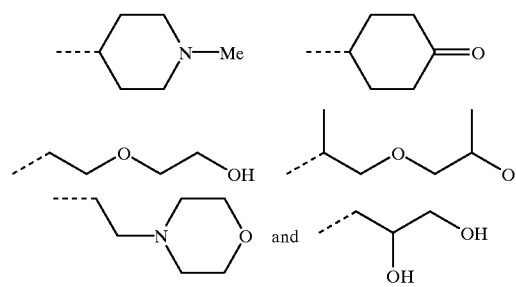

the dotted lines representing the position of the bond;

$R_5$ is selected from the group consisting of hydrogen, COR$_6$, —CO$_2$R$_6$, —SO$_2$—R$_6$, —SO$_2$NHR$_6$, —SO$_2$NHCOR$_6$, SO$_2$NHCO$_2$R$_6$, —CONH$_2$ and —CONHR$_6$, R$_6$ is selected from the group consisting of $(C_1-C_8)$-alkyl, $(C_1-C_{14})$-aryl, $(C_6-C_{14})$-aryl-$(C_1-C_6)$-alkyl, $(C_5-C_{14})$-heteroaryl, $C_5-C_{14})$-heteroaryl-$(C_1-C_6)$-alkyl, $(C_3-C_{20})$ (mono-, bi- or tri-)-cycloalkyl and $C_3-C_{20})$ (mono-, bi- or tri-)-cycloalkyl-$(C_1-C_6)$-alkyl, the aryl or heteroaryl radical being unsubstituted or substituted by 1 to 3 $R_3$;

$R_7$ is selected from the group consisting of hydrogen, $(C_1-C_6)$-alkyl-O—CO—, hydroxyl, $(C_1-C_6)$-alkyl-O—CO—O and nitro;

$R_8$ is selected from the group consisting of hydrogen, halogen and alkoxy of 1 to 6 carbon atoms;

$R_{12}$ is hydrogen or alkyl of 1 to 6 carbon atoms;

m is equal to 0, 1, 2 or 3;

n is equal to 1, 2 or 3;

said compounds of formula I being in all their possible isomeric forms, alone or in a mixture in any ratio, the alkyl aminoguanidine group adjacent to the phenyl being in para or meta position to the oxygen, or their physiologically acceptable salts.

2. A compound of claim 1 corresponding to the formula

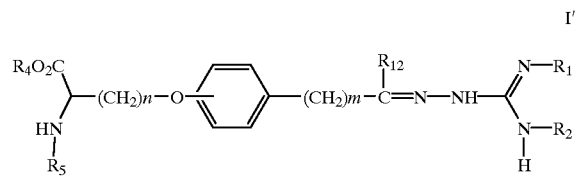

wherein $R_1$ and $R_2$ are hydrogen or together form a saturated or unsaturated divalent alkylene of 2 to 5 carbon atoms, said alkylene being unsubstituted or substituted by at least one member of the group consisting of halogen, $(C_1-C_6)$-alkyl, $(C_1-C_6)$-alkoxy, $(C_6-C_{14})$-aryl, $(C_{16}-C_{14})$-aryl-$(C_1-C_6)$-alkyl, $(C_5-C_{14})$-heteroaryl, $(C_5-C_{14}$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said alkylene able to be attached by the carbon—carbon bond to a carbocycle or a heterocycle containing 1 or 2 nitrogen atoms, with 5 to 7 ring members, saturated or unsaturated, unsubstituted or substituted by 1 to 2 $R_3$ $R_3$ is a member of the group consisting of alkyl or alkoxy of 1 to 6 carbon atoms;

$R_4$ is a member of the group consisting of hydrogen alkyl of 1 to 6 carbon atoms unsubstituted or substituted by a member of the group consisting of $(C_1-C_4)$-alkoxy, $(C_1-C_4)$-alkyl-SO$_2$— and —NR$_9$R$_9$', R$_9$ and R$_9$' are independently hydrogen or $(C_1-C_4)$-alkyl, $R_5$ is a member of the group consisting of hydrogen, —CO$_2$R$_6$, —SO$_2$R$_6$, —SO$_2$NHR$_6$ and —SO$_2$NHCO$_2$R$_6$, R$_6$ is a member of the group consisting of $(C_1-C_6)$-alkyl, naphthyl, unsubstituted or substituted by R$_3$, cycloalkyl of 3 to 12 carbon atoms, $(C_3-C_{12})$-cycloalkyl-$(C_1-C_6)$-alkyl, and

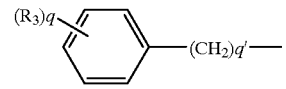

in which the R$_3$ can be different, and can be substituted at any position of the phenyl, q and q' are equal to 0 or 1;

$R_{12}$ is hydrogen or alkyl of 1 to 6 carbon atoms, m is equal to 0, 1, 2 or 3;

n is equal to 1, 2 or 3; said compounds of formula I' being in all their possible isomeric forms, alone or in a mixture in any ratio, the (alkyl) iminoguanidine group adjacent to the phenyl being in para or meta position to the oxygen, or their physiologically acceptable salts.

3. A compound of claim 2 wherein $R_1$ and $R_2$ are hydrogen, or together form a saturated or unsaturated divalent alkylene of 2 to 4 carbon atoms, said alkylene being unsubstituted or substituted by one or two members of the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl, $(C_3-C_{12})$-cycloalkyl-$(C_1-C_6)$-alkyl and oxo, said alkylene being able to be attached by the carbon—carbon bond to a carbocycle or a heterocycle containing 1 to 2 nitrogen atoms, with 5 to 7 ring members, saturated or unsaturated, unsubstituted or substituted by 1 to 3 $R_3$;

$R_3$ is alkyl or alkoxy of 1 to 5 carbon atoms;

$R_4$ is hydrogen or alkyl of 1 to 6 carbon atoms;

$R_5$ is a member of the group consisting of hydrogen, $-CO_2R_6$, $-SO_2R_6$ and $-SO_2NHCO_2R_6$, $R_6$ is a member of the group consisting of $(C_1-C_8)$-alkyl, naphthyl, unsubstituted or substituted by $R_3$, cycloalkyl of 3 to 12 carbon atoms, $(C_3-C_{12})$-cycloalkyl-$(C_1-C_6)$-alkyl and

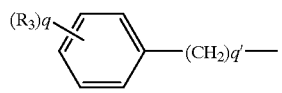

in which the $R_3$ can be different, and can be situated at any position of the phenyl, q and q' are equal to 0 or 1;

$R_{12}$ is hydrogen or alkyl of 1 to 6 carbon atoms;

m is equal to 0, 1, 2 or 3;

n is equal to 1, 2 or 3;

said compounds of formula I being in all their possible isomeric forms, alone or in a mixture in any ratio, the (alkyl) iminoguanidine group adjacent to the phenyl being in para or meta position to the oxygen or their physiologically acceptable salts.

4. A compound of the formula (I') as defined in claim 2 wherein $R_1$ and $R_2$ are hydrogen, or together form a saturated or unsaturated divalent alkylene of 2 to 3 carbon atoms, said alkylene being non-substituted or substituted by none or two members of the group consisting of halogen, $(C_1-C_6)$-alkyl, $(C_1-C_6)$-alkoxy, $(C_6-C_{14})$-aryl, $(C_6-C_{14})$-aryl-$(C_1-C_6)$-alkyl, $(C_5-C_{14})$-heteroaryl, $(C_5-C_{14})$-heteroaryl-$(C_1-C_6)$-alkyl, $(C_3-C_{12})$-cycloalkyl and $(C_3-C_{12})$-cycloalkyl-$(C_1-C_6)$-alkyl and oxo, said alkylene being able to stand to be attached by a carbon—carbon bond to a carbocycle or a heterocycle with 1 or 2 nitrogens, with 5 to 7 ring members, saturated or unsaturated, non-substituted or substituted by $R_3$;

$R_3$ is alkyl or alkyloxy of 1 to 6 carbon atoms;

$R_4$ is hydrogen or alkyl of 1 to 6 carbon atoms;

$R_5$ is selected from the group consisting of hydrogen, $-CO_2R_6$, $-SO_2R_6$, $-SO_2NHR_6$ and $-SO_2NHCO_2R_6$, $R_6$ is selected from the group consisting of -alkyl, naphthyl, non-substituted or substituted by $R_3$, cycloalkyl of 3 to 12 carbon atoms, $(C_3-C_{12})$-cycloalkyl-$(C_1-C_6)$-alkyl and

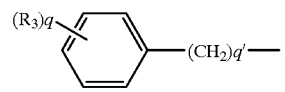

II wherein $R_3$ is individually selected at any position of the phenyl, q and q' are equal to 0 or 1;

$R_{12}$ is hydrogen or alkyl of 1 to 6 carbon atoms;

m is an integer qual to 1 or 2;

n is an integer equal to 2;

said compounds of formula (I) being in all their possible isomer forms, alone or in a mixture in any ratio, the (alkyl) iminoguanidine group adjacent to the phenyl being in para or meta position of the oxygen, or their pharmaceutically acceptable salts.

5. A compound of formula (I) of claim 1 wherein $R_5$ is $-CO_2R_6$, $R_6$ being as defined in claim 1, said compounds of formula (I) being in all their possible isomer forms, alone or in a mixture in any ratio, the (alkyl) iminoguanidine group adjacent to the phenyl being in para or meta position of the oxygen, or their pharmaceutically acceptable salts or prodrugs thereof.

6. A compound of formula (I) of claim 1 wherein $R_5$ is $-SO_2R_6$, $R_6$ being as defined in claim 1, said compounds of formula (I) being in all their possible isomer forms, alone or in a mixture in any ratio, the (alkyl) iminoguanidine group adjacent to the phenyl being in para or meta position of the oxygen, or their pharmaceutically acceptable salts.

7. A compound of formula (I) of claim 1 when $R_5$ is $-SO_2NHCO_2R_6$, $R_6$ being as defined in claim 1, said compounds of formula (I) being in all their possible isomer forms, alone or in a mixture in any ration, the (alkyl) iminoguanidine group adjacent to the phenyl being in para or meta position of the oxygen, or their pharmaceutically acceptable salts.

8. A compound of formula (I) of claim 1 selected from the group consisting of O-[4-[3-[(4,5-dihydro-1H-imidazol-2-yl)hydrazono]butyl]-phenyl]-N-[(phenylmethoxy)carbonyl]-homoserine, O-[4-[3-[(aminoiminomethyl)hydrazono]butyl]phenyl]-N-[(phenylmethoxy)carbonyl]-homoserine, O-[4-[3-[(4,5-dihydro-1H-imidazol-2-yl)hydrazono]propyl]-phenyl]-N-[(phenylmethoxy)carbonyl]-homoserine, O-[4-[3-[(aminoiminomethyl)hydrazono]propyl]phenyl]-N-[(phenylmethoxy)carbonyl]-homoserine, O-[4-[2-[(4,5-dihydro-1H-imidazol-2-yl)hydrazono]propyl]-2-methoxyphenyl]-N-[(phenylmethoxy)carbonyl]-homoserine, O-[4-[2-[(4,5-dihydro-1H-imidazol-2-yl)hydrazono]propyl]-2-fluorophenyl]-N-[(phenylmethoxy)carbonyl]-homoserine, O-[3-[3-[(aminoiminomethyl)hydrazono]butyl]phenyl]-N-[(phenylmethoxy)carbonyl]-homoserine, O-[3-[3-[(4,5-dihydro-1H-imidazol-2-yl)hydrazono]butyl]-phenyl]-N-[(phenylmethoxy)carbonyl]-homoserine, O-[3-[2-[(4,5-dihydro-1H-imidazol-2-yl)hydrazono]propyl]-phenyl]-N-[(phenylmethoxy)carbonyl]-homoserine, O-[3-[3-[(aminoiminomethyl)hydrazono]propyl]phenyl]-N-[(phenylmethoxy)carbonyl]-homoserine, O-[3-[3-[(4,5-dihydro-1H-imidazol-2-yl)hydrazono]propyl]-phenyl]-N-[(phenylmethoxy)carbonyl]-homoserine, and O-[4-[(4,5-dihydro-1H-imidazol-2-yl)hydrazono]methyl]-phenyl]-N-[(phenylmethoxy)carbonyl]-homoserine, or and their pharmaceutically acceptable salts.

9. A process for the preparation of a compound of formula (I) of claim 1 comprising reacting an acyl or formyl of formula

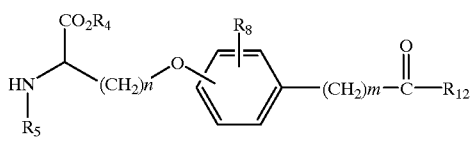
III wherein $R_4$, $R_5$, $R_8$, $R_{12}$, n and m are as defined in claim 1, and where, optionally, the functional groups are in the form of precursors or in protected form, with an aminoguanidine of the formula

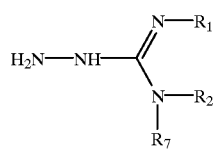
IV wherein $R_1$, $R_2$ and $R_7$ are as defined in claim 1, and where, optionally, the functional groups are in the form of precursors or in protected form, said functional groups optionally present in the form of precursors or in protected form, being subsequently converted to groups present in the compounds of formula (I).

10. A composition for treating osteoporosis comprising an amount of a compound of claim 1 sufficient to treat osteoporosis and an inert, pharmaceutical carrier.

11. A method of treating osteoporosis in warm-blooded animals comprising administering to warm-blooded animals in need thereof an amount of a compound of claim 1 sufficient to treat osteoporosis.

12. A method of inhibiting growth of tumors or cancerous metastases in warm-blooded an animals comprising administering to warm-blooded animals in need thereof an amount of a compound of claim 1 sufficient to inhibit growth of tumors or cancerous metastases.

* * * * *